(12) United States Patent
Hajj-Hassan et al.

(10) Patent No.: US 8,263,986 B2
(45) Date of Patent: Sep. 11, 2012

(54) OPTICALLY INTERROGATED SOLID STATE BIOSENSORS INCORPORATING POROUS MATERIALS—DEVICES

(75) Inventors: Mohamad Hajj-Hassan, Montreal (CA); Vamsy Chodavarapu, Saint Laurent (CA); Sam Musallam, Montreal (CA)

(73) Assignee: The Royal Institution for the Advancement of Learning/McGill University, Montreal (CA)

( * ) Notice: Subject to any disclaimer, the term of this patent is extended or adjusted under 35 U.S.C. 154(b) by 116 days.

(21) Appl. No.: 12/827,216

(22) Filed: Jun. 30, 2010

(65) Prior Publication Data
US 2011/0024771 A1 Feb. 3, 2011

Related U.S. Application Data

(60) Provisional application No. 61/222,525, filed on Jul. 2, 2009.

(51) Int. Cl.
*H01L 31/0232* (2006.01)
(52) U.S. Cl. ........... 257/84; 257/14; 257/E21.002; 257/E21.215; 257/E33.077; 438/24; 438/706
(58) Field of Classification Search .............. 257/14, 257/84; 438/24, 706
See application file for complete search history.

(56) References Cited

U.S. PATENT DOCUMENTS
2005/0218398 A1* 10/2005 Tran .................... 257/14
* cited by examiner

*Primary Examiner* — Dung A. Le
(74) *Attorney, Agent, or Firm* — Perley-Robertson, Hill & McDougall LLP/s r l

(57) ABSTRACT

Quantitative understanding of neural and biological activity at a sub-millimeter scale requires an integrated probe platform that combines biomarker sensors together with electrical stimulus/recording sites. Optically addressed biomarker sensors within such an integrated probe platform allows remote interrogation from the activity being measured. Monolithic or hybrid integrated silicon probe platforms would beneficially allow for accurate control of neural prosthetics, brain machine interfaces, etc as well as helping with complex brain diseases and disorders. According to the invention a silicon probe platform is provided employing ultra-thin silicon in conjunction with optical waveguides, optoelectronic interfaces, porous filter elements, and integrated CMOS circuitry. Such probes allowing simultaneously analysis of both neural electrical activities along with chemical activity derived from multiple biomolecular sensors with porous membrane filters. Such porous silicon and polymer filters providing biomolecular filtering and optical filtering being compatible with post-processing wafers with integrated CMOS electronics.

13 Claims, 18 Drawing Sheets

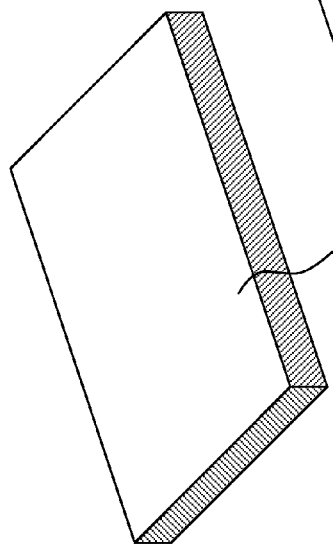
Figure 3A
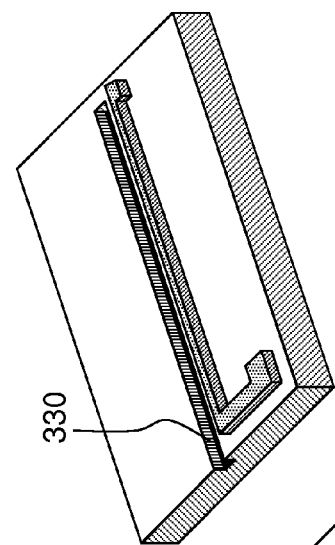
Figure 3B
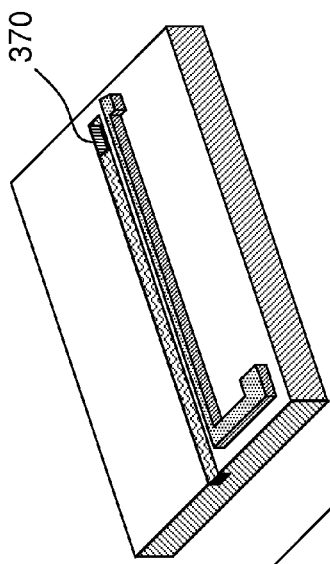
Figure 3C
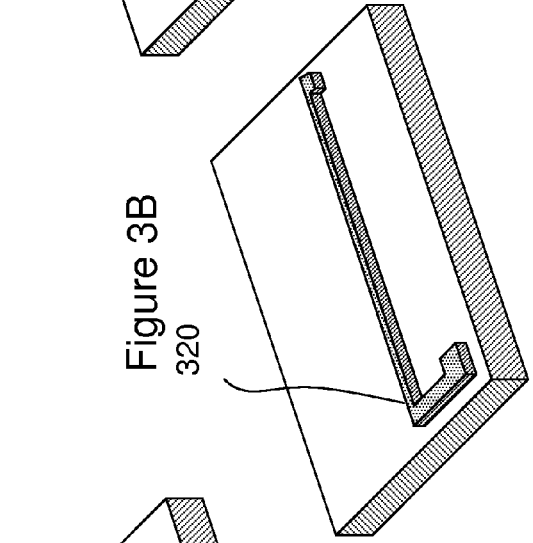
Figure 3D
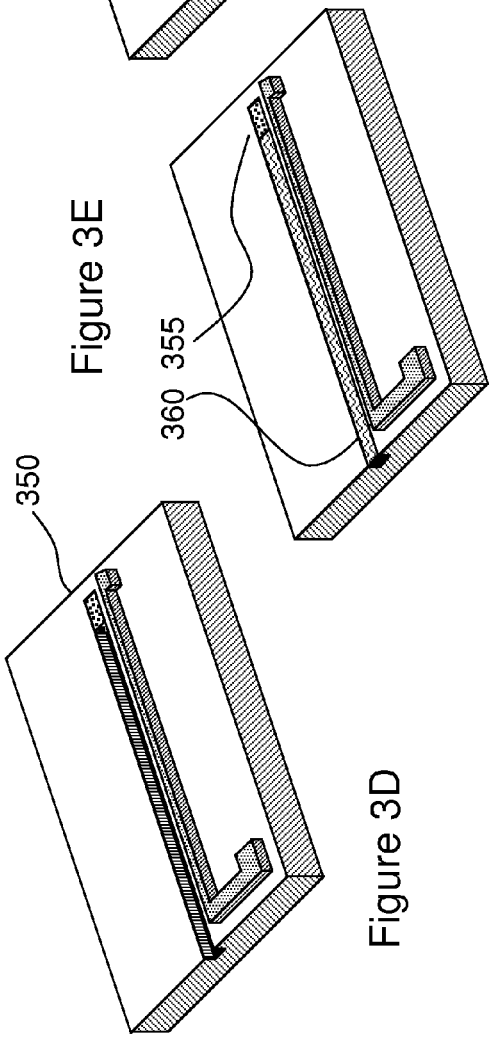
Figure 3E
Figure 3F

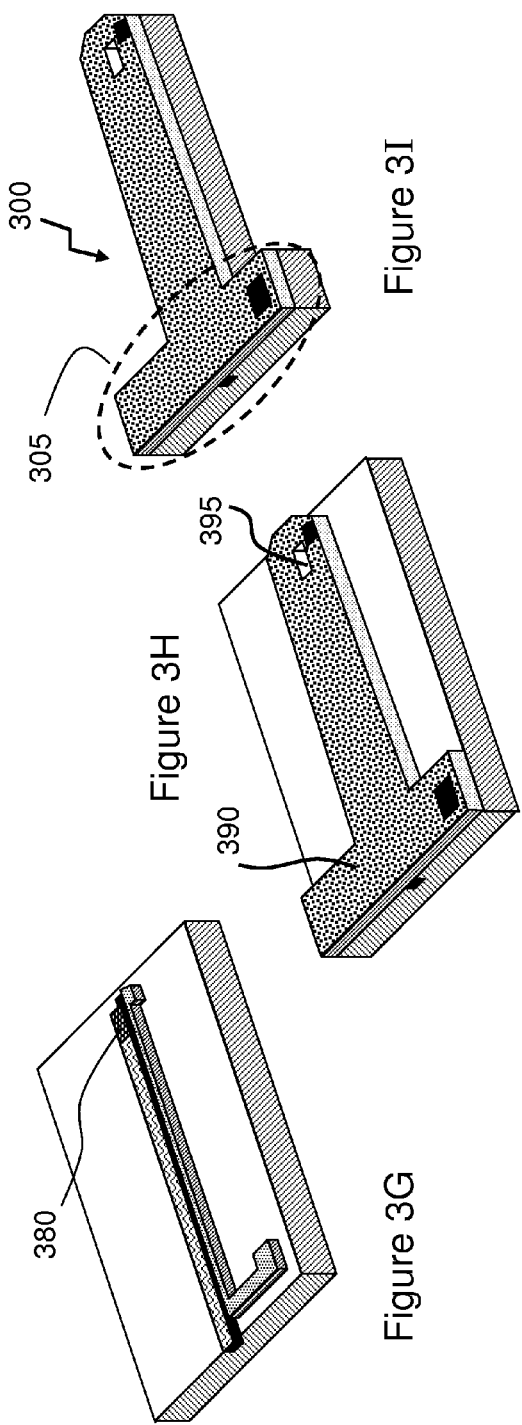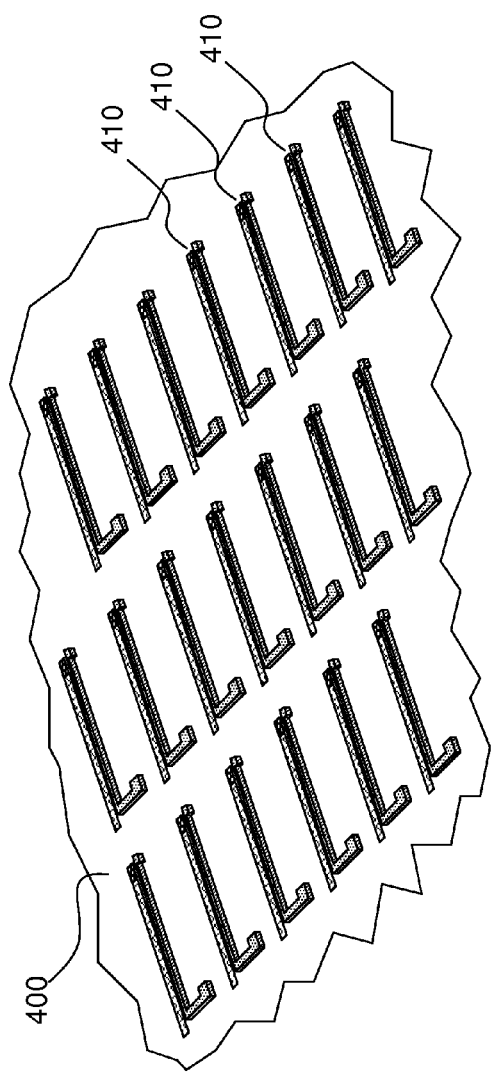

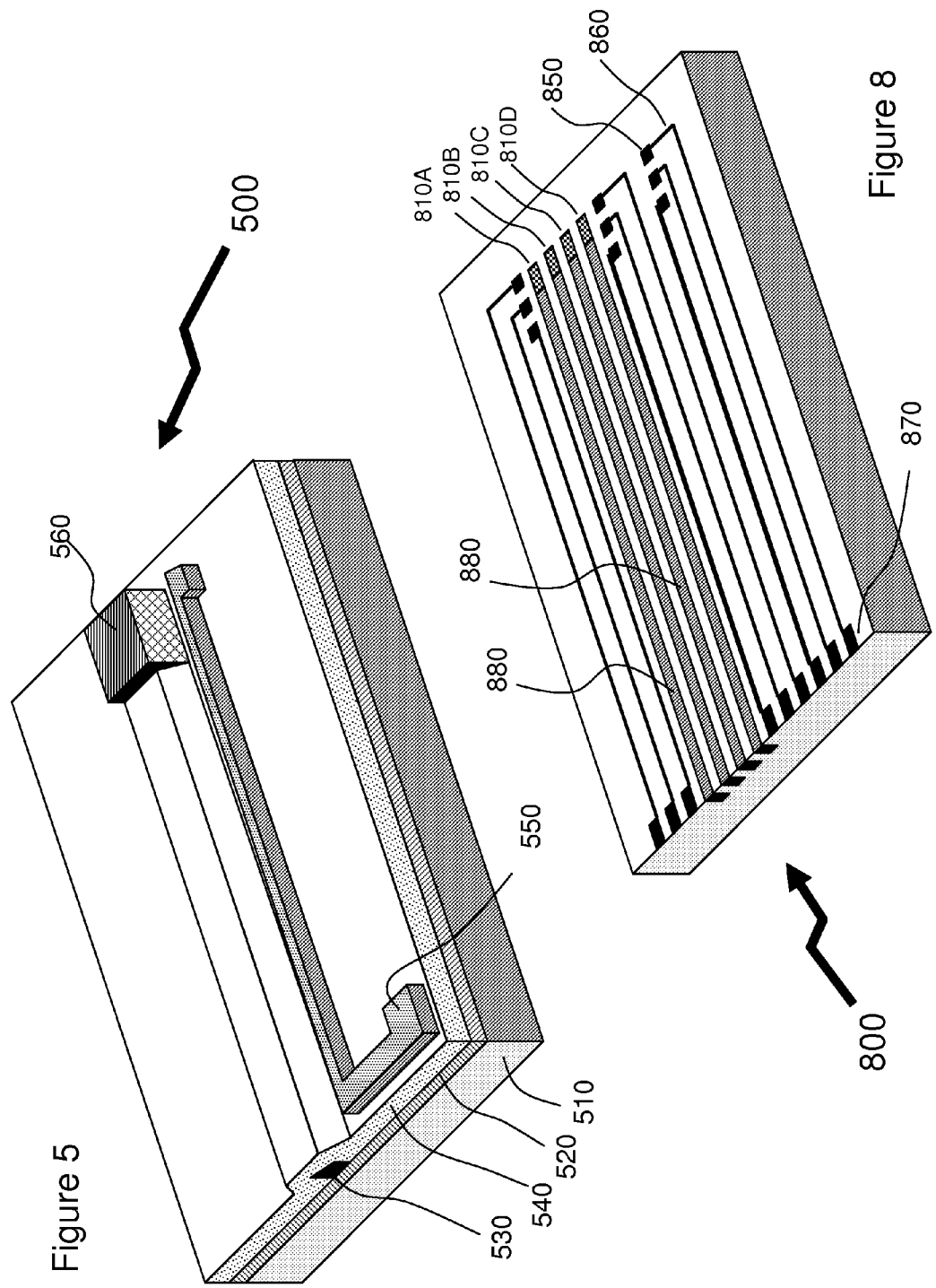

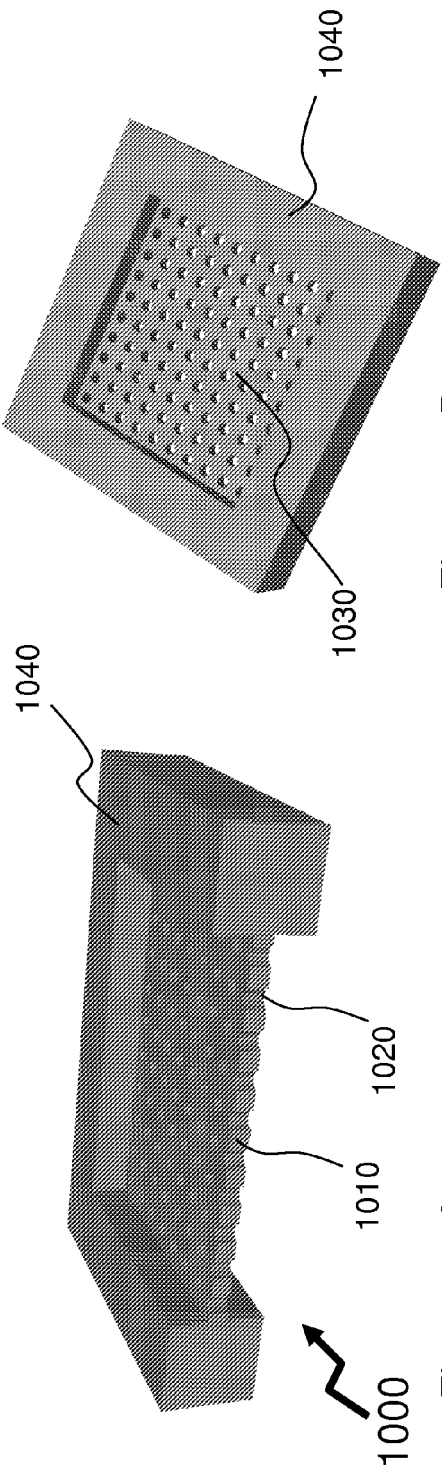
Figure 10A
Figure 10B
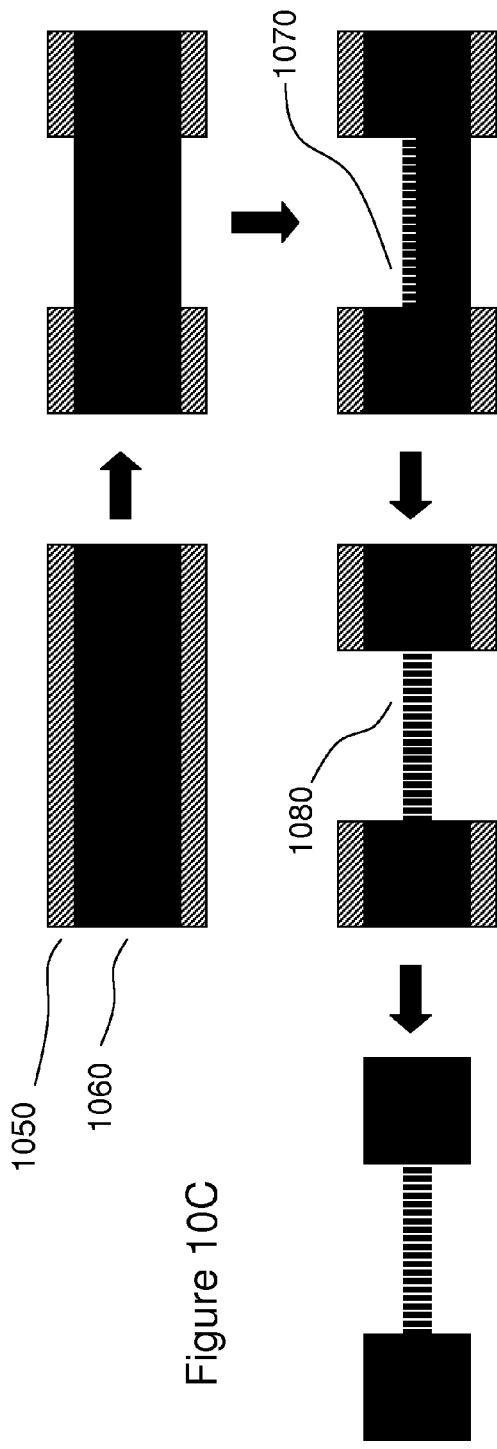
Figure 10C

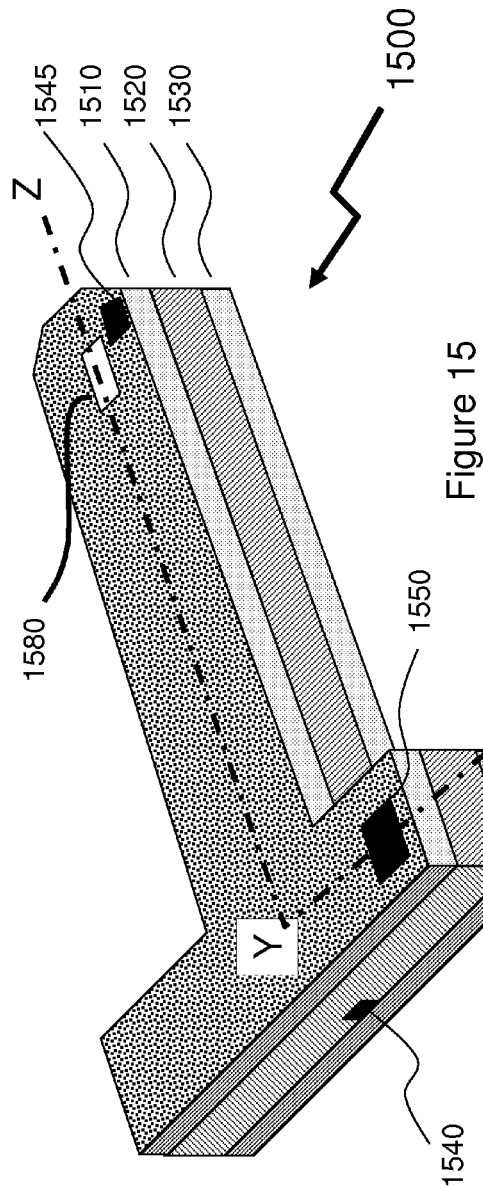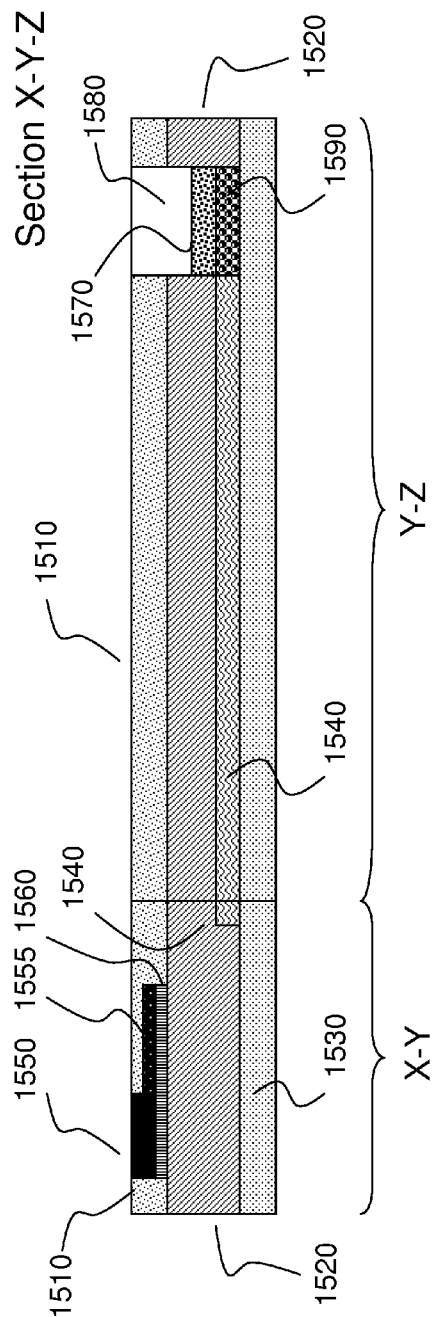
Figure 15

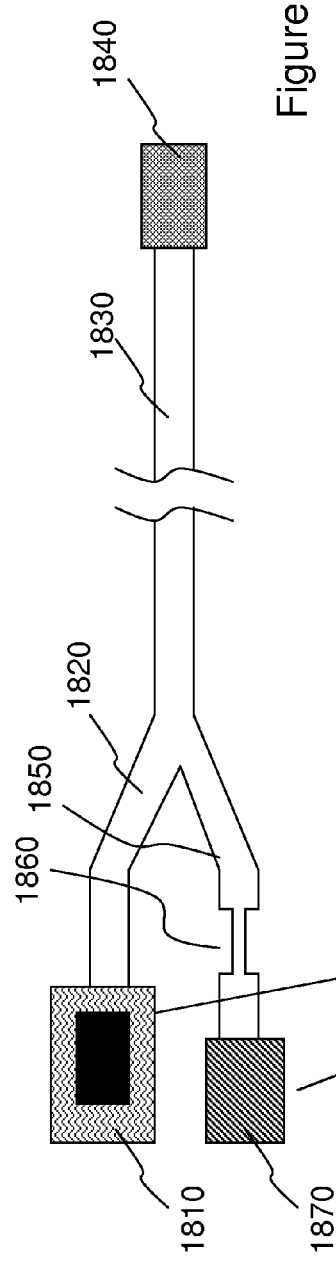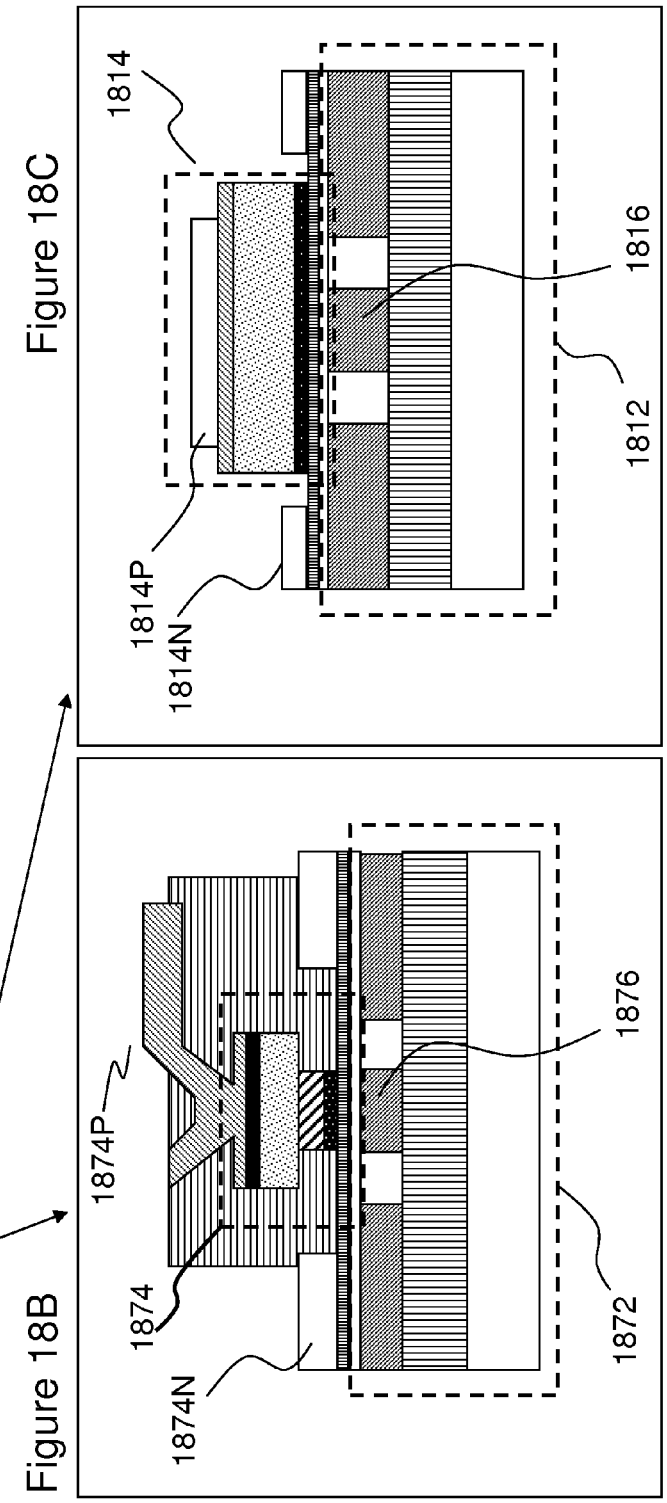

OPTICALLY INTERROGATED SOLID STATE BIOSENSORS INCORPORATING POROUS MATERIALS—DEVICES

FIELD OF THE INVENTION

This invention relates to solid state biosensors and more specifically to monolithic and hybrid integrated silicon optical biosensors employing porous silicon and porous polymer structures.

BACKGROUND OF THE INVENTION

The brain is the center of the nervous system in all vertebrate, and most invertebrate, animals. In vertebrates, the brain is located in the head, protected by the skull and close to the primary sensory apparatus of vision, hearing, balance, taste, and smell. Brains can be extremely complex. The human brain contains roughly 100 billion neurons, linked with up to 10,000 synaptic connections each. Each cubic millimeter of cerebral cortex contains roughly one billion synapses, which at an average of 1,000 synaptic connections is 1,000,000 neurons per cubic millimeter, equivalent to 100 neurons per millimeter or a neuron every 10 µm. These neurons communicate with one another by means of long protoplasmic fibers called axons and dendrites, which carry trains of signal pulses, called action potentials, to distant parts of the brain or body and target them to specific recipient cells.

Neurological ailments typically afflict patients as they age but they can present themselves at any time in an individual's lifetime. Among these ailments are Alzheimer's disease, Asperger's syndrome, cerebral palsy, Creutzfeldt-Jakob disease, Epilepsy, Fibromyalgia, Motor Neurone Disease, Parkinson's disease, Schizophrenia, Spasticity, Tourette syndrome, etc as well as more common events such as headaches, backaches, migraines, repetitive stress injuries etc. Such ailments present medical scientists with one of their greatest challenges. While research continually increases knowledge of aging and related diseases, many of the details of how the brain works (and doesn't work) remain a mystery.

Additionally paralysis, loss, or impairment of motor function due to personal accident or disease of the human nervous system reduces the ability of the affected individual to move or respond despite the capacity to think, form intentions, and make decisions. In spinal cord injuries, strokes, and diseases such as amyotrophic lateral sclerosis, the neurons that convey commands from a specific part of the brain to a desired muscle can be injured. Despite the significant strides made by basic and clinical research, few therapeutic options are available at present for restoring voluntary motor control of the limbs in patients suffering from extensive traumatic or degenerative lesions of the motor system. The prevalence of severe body paralysis is high, particularly among young adults. For instance, among the leading causes of permanent paralysis, traumatic spinal cord injuries, produced by traffic accidents, acts of violence, or falls account for nearly 11,000 new cases each year in the United States alone, see A. I. Nobunaga et al "Recent Demographic and Injury Trends in People Served by the Model Spinal Cord Injury Care Systems" (Arch. Phys. Med. Rehabil. Vol. 80 Nov. 1999, pp 1372-1382) and M. A. L. Nicolelis "Brain-Machine Interfaces to Restore Motor Function and Probe Neural Circuits" (Nature Reviews Vol. 4, May 1993, pp 417-422). The National Spinal Cord Injury Association estimates there are 450,000 people living within spinal cord injury in the United States of America alone; others put the estimate more conservatively at 250,000 costing the United States of America an estimated $9.7 billion per annum (Centers for Diseases Control and Prevention (CDC)).

About half of these patients are quadriplegic, which means that, owing to injury to the cervical spinal cord, they cannot move any of their limbs or any other muscle below the neck. Quadriplegics depend on continuous assistance to accomplish even the simplest of motor acts. Whereas most of us take for granted our ability to breathe, eat and drink, a quadriplegic patient usually cannot do any of these without the assistance of a machine (such as a ventilator) or a caretaker. For this reason, restoring even the smallest of motor skills in these patients can have a profound effect on their quality of life. Recent experimental demonstrations in rodents, primates, and patients have raised interest in the proposition that neural prosthetic devices designed to bypass spinal cord lesions could be used to restore basic motor functions in patients suffering from severe body paralysis.

Brain machine interfaces or neural prosthetics represent an engineering approach to bypass paralytic parts of human body. Implanted arrays of neural recording electrodes and electronics acquisition devices are employed to monitor in real-time the brain electrical activities or neural electropotentials that reflect the intentions of a paralyzed human. These signals are the inputs for the prosthesis or computer system they are trying to use. Software algorithms analyze these signals to form the link between recorded neural signals and the thoughts of the paralyzed patient that are decoded to drive the external robotic prosthetic devices.

In research studies the electrical stimulation of deep brain structures (deep brain stimulation, or "DBS") has been established and may be developed into an effective treatment modality for advanced Parkinson's disease and essential tremors arising therefrom. DBS is also being evaluated as a treatment for other neurological conditions and appears to be useful in the treatment of several types of dystonias and hyperkinetic disorders. While the range of clinical applications for DBS has expanded in recent years, its mechanism of action is not completely understood. In fact studies directed towards an elucidation of the physiologic underpinnings of DBS certainly have been aided by microelectrode arrays for chronic implantation into animals, including subhuman primates, and which deliver highly localized electrical stimulation into the target nucleus, and which include the capability of monitoring the response to the electrical stimulation by individual neurons in the target nucleus. It is important that such microelectrodes be able to deliver stimulation for an extended interval, and without injury to the tissue. An array of independently controllable stimulating microelectrodes distributed throughout the target nucleus would permit precise control of the spatial distribution of the stimulation, by stimulating either with single microelectrodes or with a subgroup of microelectrodes that could be pulsed either simultaneously or sequentially.

Amongst prior art microelectrodes are those based upon printed circuit board (PCB) approaches such as M. A. L. Nicolesi et al in U.S. Pat. No. 6,993,392 entitled "Miniaturized High Density Multi-Channel Electrode Array for Long-Term Neuronal Recordings" and J. C. Williams et al in U.S. Pat. No. 7,504,069 entitled "Micro Device for High Resolution Delivery and Monitoring of Stimuli to a Biological Object In-Vitro". Others reported microfilament two-dimensional arrays of flexible materials such as plastics with conductive coatings such as S. C. Jacobsen et al in US Patent Application 2007/0,167,815 entitled "Multi-Element Probe Array", whilst others have exploited machinable ceramics to form thin probes such as K. A. Moxon et al in U.S. Pat. No.

6,834,200 entitled "Ceramic Based Multi-Site Electrode Arrays and Methods for Their Production".

Silicon has also formed the basis of developments for neuronal probes due to its excellent micromachining properties, compatibility with high volume semiconductor processing techniques and the ability to integrate CMOS electronics for signal conditioning, detected signal amplification etc. Such developments including for example D. B. McCreery in US patent application entitled "Multi-Electrode Array for Chronic Deep Brain Micro-Stimulation for Recording", P. K. Campbell et al in "Silicon based 3D Neural Interface, Manufacturing Processes for a Intracortical Electrode Array" (IEEE Trans. Biomed. Eng. Vol. 38 No. 3 pp 758-768 August 1991), and D. J. Anderson in "Current and Future Uses of High Density Implant Arrays for Functional Electrical Stimulation Systems: (International Functional Electrical Stimulation Systems 2003, Keynote Address, Proc. Vol. 2 (1), September 2003).

The accurate understanding of brain functions, and potentially accurate interpretation of neurological activity in specific localized brain regions such as motor control, speech etc, requires that we have knowledge of the interaction of separate brain regions and their functional connectivity during particular cognitive or motor tasks. This requires more than simply detecting neuron activity within specific regions of the brain. There are many sources of information in addition to the electrical activities of neural communications which can be in the form of spikes or local field potentials. Included amongst these other sources of signals are neural biomarkers such as oxygen ($O_2$), acidity (pH), potassium ($K^+$) ions, and sodium ($Na^+$) ions. These signals can aid to classical techniques in decoding the distributed patterns of brain activity associated with specific motor activity. There is much evidence from functional magnetic resonance imaging (FMRI), which provides functional connectivity maps of distinct spatial distributions of temporally correlated brain regions, that tissue oxygenation is related to neural electrical activities, see for example J. K. Thompson et al in "Single-Neuron Activity and Tissue Oxygenation in the Cerebral Cortex" (Science, Vol. 299, No. 5609, February 2003, pp 1070-1072; (http://tsolab.org/jclub/20031006/freeman.pdf) and A. Devor et al in "Coupling of Total Haemoglobin Concentration, Oxygenation, and Neural Activity in Rat Somatosensory Cortex" (Neuron, Vol. 39, pp. 353-359, Jul. 17, 2003; http://www.nmr.mgh.harvard.edu/PMI/PDF/2003/Devor_Neuron_39_353_2003.pdf).

FMRI infers neural activity by measuring small changes in the de-oxygenation of hemoglobin in a cortical area. In contrast to oxygenated hemoglobin, deoxygenated hemoglobin disrupts a magnetic field which leads to an enhancement of the MRI. Faster optical imaging techniques have to be used however to assess the temporal properties of the oxygen response which represents a continuous stream of information alongside the electrical activity. Several researchers have reported that $O_2$ concentration ascribed to immediate $O_2$ consumption can be observed 100 milliseconds after activity onset, see for example A. Grinvald et al in "Non-Invasive Visualization of Cortical Columns by fMRI," (Nature Neuroscience, vol. 3, pp. 105-107, February 2000). Thus, hemodynamic events are tightly coupled to cortical electrical activity immediately following activation. $O_2$ pressure changes have also been shown to be highly specific for local increases in neuronal activity and correlated with the degree of activity.

Thus, to establish a quantitative understanding of this relationship at a sub-millimeter scale, it would be beneficial to provide an integrated probe platform to hold oxygen and/or other biomarkers' sensors along with recording sites to measure the neural electrical activity. The biomarker sensors within the integrated probe platform exploiting optical techniques alongside the electrical circuitry for the neural measurements. Such an integrated probe platform would be important for the accurate control of neural prosthetics and brain machine interfaces as well as helping in providing answers to complex brain diseases and disorders. Such a hybrid microprobe that has the capability to simultaneously record both the neural electrical activities along with chemical activity, such as $O_2$, pH, $K^+$, and $Na^+$ for example, using an optical sensor will result in a significant increase of the information yield and enhance deciphering the nature of the information flow and function when compared to standard probes that can only record electrical activities It would also be beneficial in some instances for the sensor elements to include physical biological filters such that only the specific target molecules or groups of molecules were able to interact with the sensor element. As such it would be beneficial for the integrated probe platform to include physical membrane filter elements as well as the optical interrogation elements, electronics, etc.

It would also be beneficial if the integrated probe platform was formed as a hybrid silicon circuit allowing the platform to leverage the cost benefits of high volume, large wafer silicon processing and provide opportunity for the potential integration of electrical and optical circuit elements allowing fully monolithic optically interrogated integrated sensor devices and arrays. Further for maximum flexibility hybrid integration of optical emitter and detector devices would allow a wider range of sensor materials to be employed.

SUMMARY OF THE INVENTION

It is an object of the present invention to obviate or mitigate at least one disadvantage of the prior art.

In accordance with an embodiment of the invention there is provided a device comprising a substrate, a recording site formed upon a first surface of the substrate comprising at least one of a recording pad and an interconnection electrically connected to the recording pad, and an optical sensor formed upon a second surface of the substrate comprising at least an optical waveguide and a biosensor.

In accordance with another embodiment of the invention there is provided a method comprising providing a probe, the probe comprising at least a substrate, a recording site formed upon a first surface of the substrate comprising at least a recording pad and an interconnection electrically connected to the recording pad, and an optical sensor formed upon a second surface of the substrate comprising at least an optical waveguide and a biosensor. The method further comprising that the probe provides a first output signal generated in dependence upon at least the biosensor and a first characteristic of a first predetermined portion of the medium within which the probe is placed and at least one of a second output signal generated in dependence upon at least one of a second predetermined region of the medium and the recording pad and an input signal to the second predetermined region of the medium.

In accordance with another embodiment of the invention there is provided a method comprising providing a substrate, providing a mask to a first predetermined region of the substrate, the mask exposing thereby a second predetermined region of the substrate, exposing the substrate to an etchant under predetermined conditions of at least one of pressure, time, temperature, electrical potential, and gas mixture, wherein the exposed second predetermined region of the substrate is etched to at an approximately predetermined depth and results in a porous region of the substrate.

In accordance with another embodiment of the invention there is provided a method comprising providing a substrate, providing a first mask to a first predetermined region of the substrate, the mask exposing thereby a second predetermined region of the substrate, and providing a second mask to a third predetermined region of the substrate, the mask exposing thereby a fourth predetermined region of the substrate. The method further comprising exposing the substrate to an etchant under predetermined conditions of at least one of pressure, time, temperature, electrical potential, and gas mixture, wherein the exposed second and fourth predetermined regions of the substrate are etched to at an approximately predetermined depth and result in a porous region of the substrate therebetween.

In accordance with another embodiment of the invention there is provided a method comprising providing a substrate, forming a porous region of the substrate, the porous region formed providing a first mask to a first predetermined region of the substrate, the mask exposing thereby a second predetermined region of the substrate, exposing the substrate to a first etchant under first predetermined conditions of at least one of pressure, time, temperature, electrical potential, and gas mixture. The method further comprising providing a second mask to a third predetermined region of the substrate, the mask exposing thereby a fourth predetermined region of the substrate, and exposing the substrate to a second etchant under second predetermined conditions of at least one of pressure, time, temperature, electrical potential, and gas mixture; wherein the remaining substrate material between the etched second and fourth predetermined regions comprises a porous form of the substrate.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIGS. 3A through 3I depict an exemplary manufacturing sequence for providing an embodiment of the invention for a combined electrical and optical biosensor probe;

FIG. 4 depicts a portion of a silicon wafer showing arrays of combined neuronal probes at an intermediate processing point prior to probe shaping and probe separation according to an embodiment of the invention;

FIG. 5 depicts a combined neuronal probe exploiting a silica-on-silicon optical waveguide to address the optical biosensor according to an embodiment of the invention;

FIG. 8 depicts an embodiment of the invention wherein multiple electrical contacts are employed together with an array of optical biosensors;

FIGS. 10A through 10C depict a method of forming a porous silicon membrane according to an embodiment of the invention;

FIG. 15 depicts an optically interrogated sensor probe according to an embodiment of the invention employing a porous polymer sensor element in conjunction with a porous silicon biological filter element;

FIG. 18 depicts an embodiment of the invention wherein the optical biosensor is monolithically integrated using silicon optoelectronics in conjunction with optical waveguides and porous silicon wavelength filter.

DETAILED DESCRIPTION

Figure 1C:
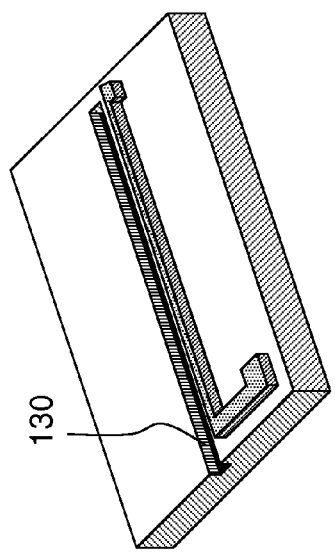
FIGS. 1A through 1I depict an exemplary manufacturing sequence for providing an embodiment of the invention for a combined electrical and optical biosensor probe.

This present invention is directed solid state biosensors and more specifically to monolithic and hybrid integrated silicon optical biosensors employing porous silicon and porous polymer structures.

Reference may be made below to specific elements, in many instances numbered in accordance with the attached figures. The discussion below should be taken to be exemplary in nature, and not as limiting of the scope of the present invention. The scope of the present invention is defined in the claims, and should not be considered as limited by the implementation details described below, which as one skilled in the art will appreciate, can be modified by replacing elements with equivalent functional elements and different processing sequences, etc.

OPTICALLY INTERROGATED SILICON PROBE: The hybrid neural probe is a microdevice that forms the connection between the biological neural tissue with external devices and electronic systems, and monitors neural electro-potentials and/or biomarkers. The electrical signal recording part of a silicon probe array consists of single or multiple long protruding tapered silicon electrodes. Each neural probe can contain multiple metallic recording sites to record brain electrical activity, interconnect traces, and back carrier area carrying the bonding pads to connect the probes to external electronics. The optical biological and chemical sensing part of the probe consists of a material or series of materials doped with analyte-specific recognition elements. These sensor materials are coated at the end of an optical waveguide structure fabricated on the silicon microelectrode which may be embedded inside the silicon microelectrode array to protect the sensors during surgical implantation. The optical waveguides providing send and receive optical signals from the biochemical sensors, which may include for example doped xerogels.

Optical sensing was adopted in the multiple measurand probes rather than the prior art amperometric-based sensors used to simultaneously measure brain tissue oxygenation and neural activity. Prior art amperometric-based probes being limited by several factors. First, complication of their fabrication in standard silicon microfabrication processes limits their widespread acceptance. Second, the growing need for ultra-long silicon microelectrodes to access deeper regions of the brain further complicates the microfabrication process. These two factors thereby combine to reduce manufacturing yields, increase processing complexity and thereby reduce manufacturing costs. Additionally optical sensors do not consume oxygen during measurement and do not pose the danger of accidental poisoning during use, a risk that exists with amperometric-based sensors. Further amperometric-based sensors are temperature sensitive requiring additional calibration and sensors for accurate measurements and subject to fouling due to deposition of biological material on the cathode may limit the life of the electrochemical based sensor.

Amongst optical sensing processes that can be utilized are those based on luminescence spectroscopy which is a widely used technique to implement rapid, high throughput, and highly selective and sensitive biochemical sensors. For example, sol-gel derived xerogel materials are an excellent class of nanomaterials suitable for encapsulation of optically-active biochemical recognition elements. As such these host sol-gel media have nano-/micro-scale caged-like networked structures that bind and/or house the biochemical recognition elements. Xerogel materials offer a number of advantages including simple ambient temperature processing, relative stability for long periods of time, optical transparency in visible wavelengths region, biocompatibility, electrically insulating, and, more importantly, compatibility with a variety of recognition elements. Optical waveguides are used to transport the excitation light, for example from circuitry in the back carrier area of the probe that may be outside the brain to inside to excite the recognition elements either from optoelectronic elements coupled in hybrid manner to the optical waveguides or monolithically integrated within the back carrier area for example. Once excited, these biochemical luminophores emit light which will be quenched by the molecules of the target analyte. For example, the recognition element may be chosen to be sensitive to oxygen in order to monitor the oxygen concentration, blood oxygen level dependant (BOLD) signal, in the brain. A portion of the emitted light from the luminphores is conveyed back along the probe from the small tip end to the back carrier area.

It would be apparent to one skilled in the art that the human brain has neuronal activity that may be required to be monitored and/or excited throughout its entire structure. Accordingly the distance from probed locations to the external cranium may range from only a few millimeters to approximately a hundred millimeters. As the intrusion into the brain should be minimized as much as possible it is beneficial to reduce the thickness of the probes as much as possible. This results in the use of ultra-thin silicon formed into long thin probes, of width potentially of only tens of microns at the tip that may be a hundred millimeters long. It is therefore necessary to structurally reinforce the probes to increase their physical integrity and length as well as increasing their functionality and sensor density. As will be taught below regions of the electrodes that are more susceptible to breakage to withstand the insertion axial forces, retraction forces, and tension forces of the brain tissue during surgical implantation are reinforced. The probe stability being improved by adding a stiff longitudinal reinforcing structure of suitable cross-section at the middle of the probe which pushes the region of maximum stress from the middle of the probe to the base region of the probe close to the base carrier area, which is typically sturdier.

Figure 1F:
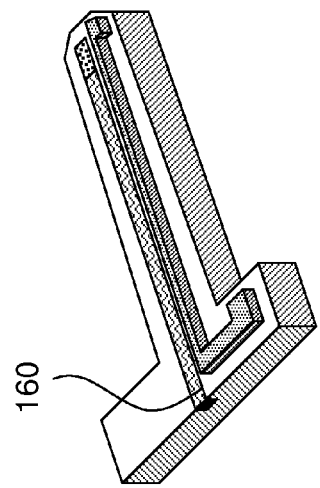
Figure 1B:
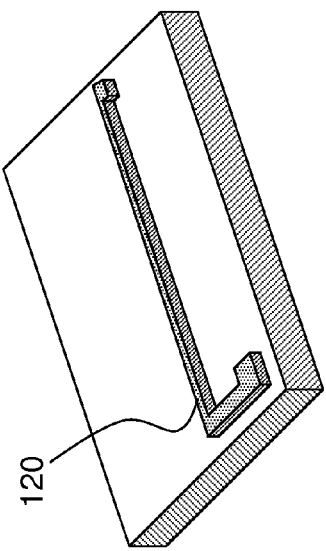
Figure 1E:
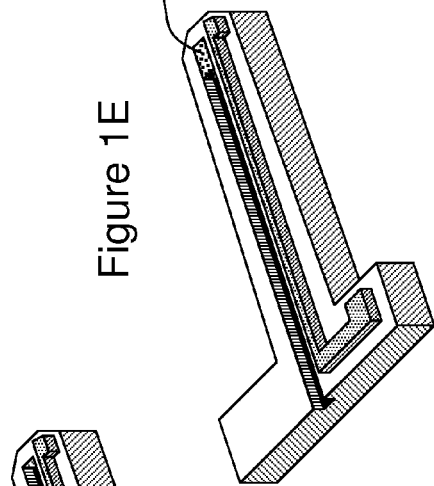
Figure 1A:
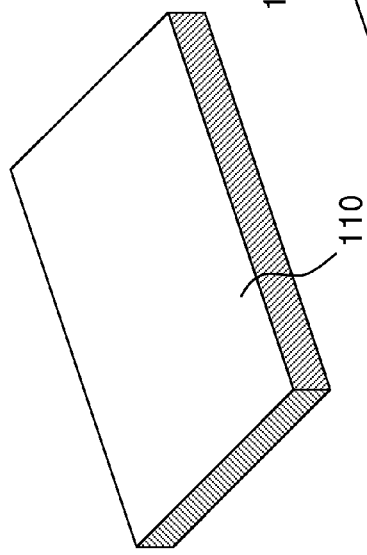
Figure 1D:
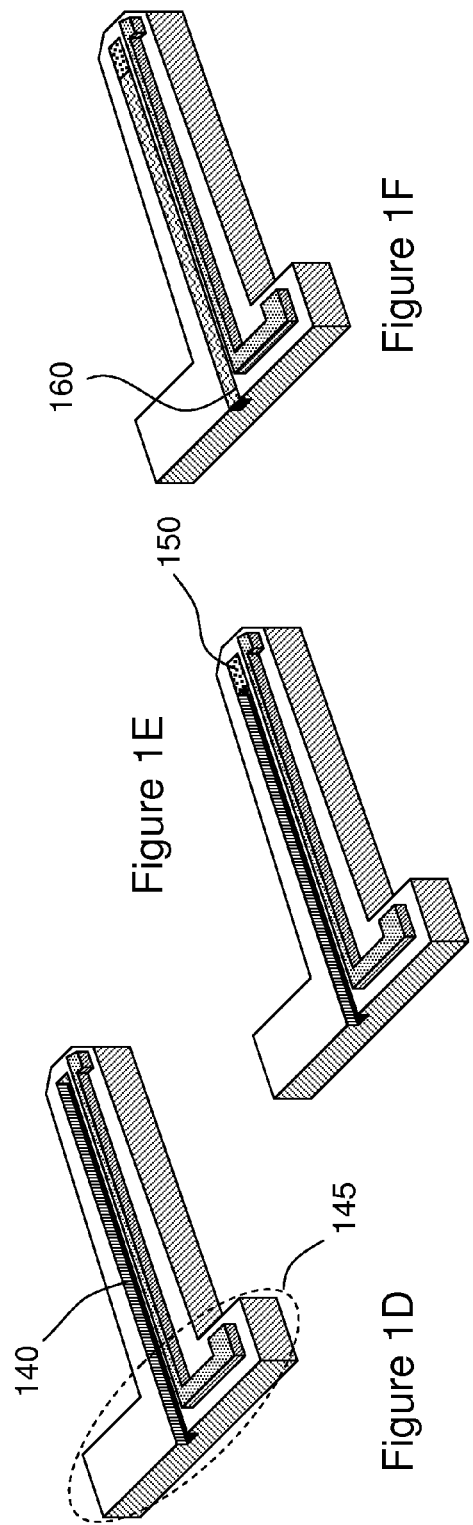
Figure 1G:
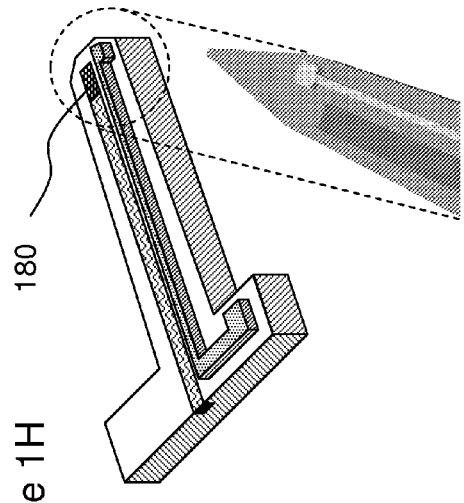
Figure 1I:
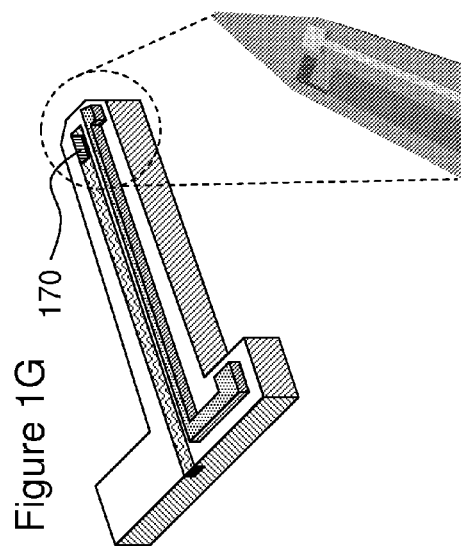

Referring to FIG. 1A through to FIG. 1I there is shown an exemplary process flow for the manufacturing a multiple measurand brain probe according to an embodiment of the invention. The process starts in FIG. 1A with sub-dicing a 100 microns thick 4" diameter double side polished silicon wafer into an individual silicon die 110, for example using a dicing saw or by a scribe-and-cleave technique. Within this embodiment of the invention the silicon wafer is boron doped with a resistivity of 20 ohm-cm and having a <100> orientation. Next in FIG. 1B a 20 nm thin layer of titanium is deposited by sputtering. This layer serves as an adhesion layer between the silicon die 110 and the subsequent 100 nm thick gold layer deposited on the titanium also by sputtering forming electrode metallization 120. These metal layers are patterned by photolithography and etching to form the recording sites, interconnections and bond pads.

Subsequently a resist layer is patterned with photolithography and the exposed silicon etched using an anisotropic $XeF_2$ or deep reactive ion etch (DRIE) system to form a rectangular cavity, for example a 100 μm wide rectangular cavity of depth 20 μm. This being shown in FIG. 1C. Next a second photolithographically patterned resist layer is used to define the probe electrode. The exposed silicon is etched completely by $XeF_2$ system or DRIE which results in a tapered probe electrode 140 as shown in FIG. 1D with wide base carrier area 145. Next using a direct-dispense automated robotic technique, a drop of organic ink 150 consisting of a composite of petroleum jelly and microcrystalline wax, is extruded through a micro-nozzle and deposited over a predetermined region of the rectangular cavity 130 at the top of the probe as shown in FIG. 1E. This drop of organic ink 150 acting to serve as a sacrificial layer subsequently.

Figure 1H:
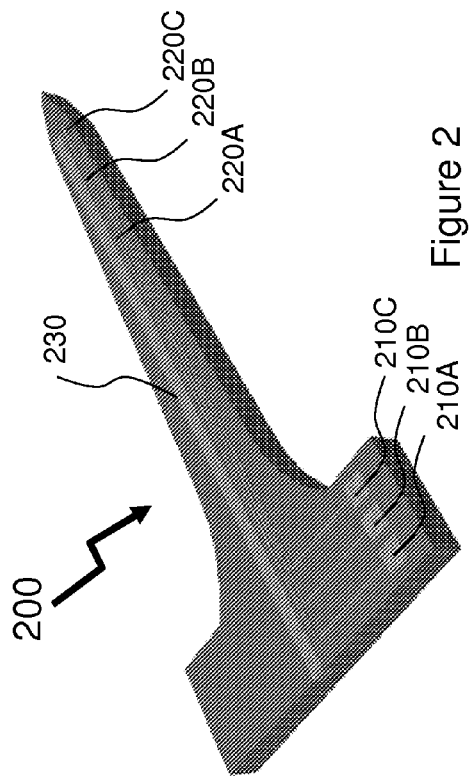

Using the same direct-dispense technique, the rest of the rectangular cavity 130 is filled-up with a polymer 160 to form the optical waveguide as shown in FIG. 1F. Next the organic ink 150 is then melted at 65° C. and extracted, leaving behind the polymeric waveguide with a sensor cavity 170 as shown in FIG. 1G. Then as shown in FIG. 1H this direct-dispense robotic technique is employed to fill the sensor cavity 170, left from the extraction of the organic ink 150, with the appropriate xerogel sensing material 180. Finally the probe is coated with Parylene™ C 190, a chemical vapor deposition compatible poly-xylylene polymer with chlorine, and patterned in order to expose the xerogel sensing material 180 through opening 195, a recording site 196, and a bond pad 197. Parylene™ C 190 being approved by the US Food and Drug Administration (FDA).

It would be apparent to one skilled in the art that the process flow presented supra whilst operating upon a discrete silicon die 110 and employing robotic dispensing of the polymer 160, organic ink 170 and Xerogel sensing material 180 does allow the probe to be manufactured directly on ultrathin silicon, such as the 100 microns identified supra but also thinner, down to 10 microns for example. Further whilst the exemplary process has been described with respect to a boron doped substrate and the $XeF_2$ etch, the silicon substrate may be of any doping from N doped through undoped to P doped as the $XeF_2$ etch etches indiscriminately with respect to resistivity or type of doping.

Figure 2:
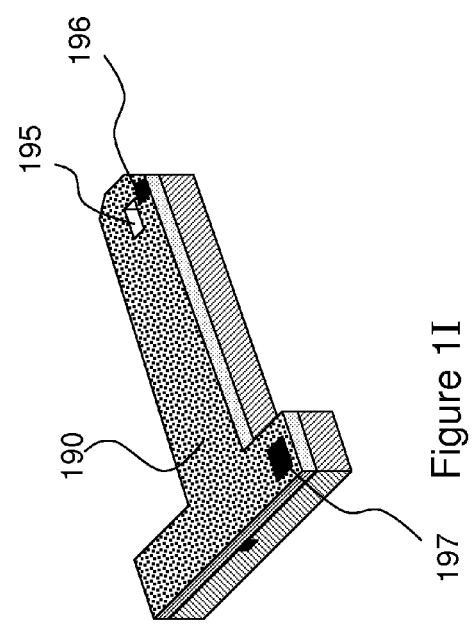
FIG. 2 depicts an embodiment of the invention wherein multiple electrical contacts are provided alongside an optical biosensor.

Referring to FIG. 2 there is shown a probe 200 comprising optical waveguide 230, first, second and third bonding pads 210A, 210B and 210C respectively which are connected via electrode traces to first, second, and third measurement sites 220A, 220B and 220C respectively. As neurons range in dimension between 10 microns to 50 microns then it would be evident that the optical waveguide 230, for example formed as discussed supra in respect of FIGS. 1A through 1I, with width 20 um is of a dimension comparable to that of the neurons where the oxygenation is being measured. Equally the measurement sites may be similarly dimensioned to that of the neurons, and accordingly placed in a predetermined two-dimensional array as desired across the width and length of the probe 200.

Referring to FIG. 3A through to 3I there is shown an exemplary process flow for the manufacturing a multiple measurand brain probe according to an embodiment of the invention. The process beginning in FIG. 3A with the provisioning of a 100 microns thick 4" diameter double side polished silicon wafer 310. Within this embodiment of the invention the silicon wafer is boron doped with a resistivity of 20 ohm-cm and having a <100> orientation. Next in FIG. 3B a 20 nm thin layer of titanium is deposited by sputtering. This layer serves as an adhesion layer between the silicon die 310 and the subsequent 100 nm thick gold layer deposited on the titanium also by sputtering forming electrode metallization 320. These metal layers are patterned by photolithography and etching to form the recording sites, interconnections and bond pads.

Subsequently a resist layer is patterned with photolithography and the exposed silicon is etched using an anisotropic $XeF_2$ or DRIE system to form for example a 100 μm wide rectangular cavity 330 of depth 20 μm. This being shown in FIG. 3C. Next in FIG. 3D a second photolithographically patterned resist layer is used to protect the region 350 within the rectangular cavity 330 which will subsequently contain the biosensor.

Using a third photolithography stage the remainder of the rectangular cavity 330 is filled with a polymer 360 to form the optical waveguide as shown in FIG. 3E. Next the second photolithographically patterned resist layer is removed leaving behind polymeric waveguide with a sensor cavity 370 as shown in FIG. 3F. Then using a fourth photolithographic process the sensor cavity 370 is filled within the appropriate xerogel sensing material 380 as shown in FIG. 3G. Finally the probe is coated with Parylene™ C 390, a chemical vapor deposition compatible poly-xylylene polymer with chlorine, and patterned in order to expose the oxygen sensing xerogel 380 through opening 395 as shown in FIG. 3H.

A xerogel being beneficial for hosting the active biosensor material due to retained high porosity (typically 25%), large surface area (150-900 $m^2/g$); along with very small pore size (1-10 nm). Next as shown in FIG. 3I the structure is patterned by etching the exposed silicon completely by $XeF_2$ or DRIE systems which result in a tapered probe 300 as shown in FIG. 3I with wide base carrier area 305. If the tapered probe 300 is formed in a row then the individual tapered probes 300 may also be separated by dicing or cleaving.

Alternatively the silicon wafer 310 may be a 6" or 8" wafer either processed as an ultra-thin wafer or as a thicker wafer which is processed either at the end of the process flow or at an intermediate processing point using chemical-mechanical planarization. It would also be possible to employ silicon crack propagation as reported by IMEC (http://www.sciencedaily.com/releases/2008/07/080714144222.htm) wherein a full thickness silicon wafer once processed has a crack induced approximately 30 microns deep into the structure and is propagated across the wafer. Similarly epitaxial lift off of epitaxially grown silicon on porous silicon has been demonstrated for removal of large area ultra-thin silicon (http://www.imec.be/wwwinter/mediacenter/en/SR2003/scientific_results/research_imec/2_4_photo/2_4_2/2_4_2_1.html).

The process flow depicted in FIGS. 3A through 3I differs from the first process flow depicted in FIGS. 1A through 1I in that the processing of the probes is undertaken at the wafer level until the $XeF_2$ or DRIE formation of the tapered probes 300 and their separation. Accordingly all manufacturing processes prior separation of the tapered probes 300 are performed on arrays of devices such as shown in FIG. 4 wherein the probes 410 are formed in array across the substrate 400 It would be evident to one skilled in the art that different process flows may be implemented without departing from the invention. For example the direct-dispense technique may be used to deposit the xerogel where the selected xerogel is not compatible with semiconductor processing.

Referring to FIG. 5 there is shown another embodiment of the invention for a probe 500. In contrast to tapered probe 300 which employs a polymer waveguide, formed from rectangular cavity 330 and polymer 360, probe 500 employs a silica-on-silicon waveguide. As such the probe 500 comprises substrate 510, lower cladding 520, core 530, and upper cladding 540 which are used to form the optical waveguide. The probe 500 further constitutes xerogel 560 and electrode 550. The core 530 being deposited, patterned and etched prior to overcoating with the upper cladding 540. It would be apparent to one skilled in the art that other waveguide technologies may be employed to form the optical waveguide structure, including for example silicon-on-insulator, polymer, and silicon oxynitride.

Figure 6B:
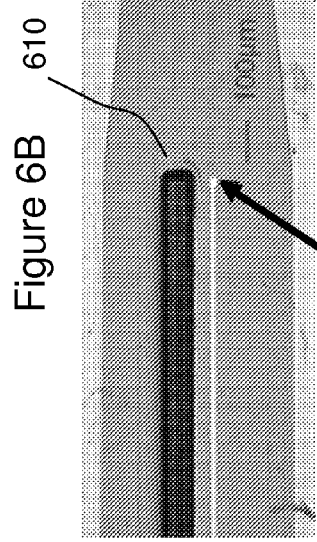
FIG. 6A and 6B depict optical micrographs of the bond pad and electrode regions of a combined neuronal probe during processing according to an embodiment of the invention.
Figure 6A:
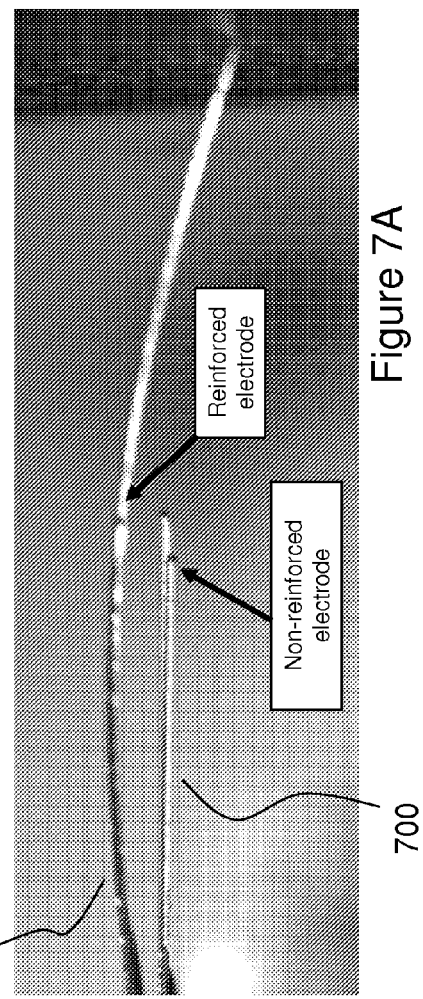

Referring to FIGS. 6A and 6B there are shown optical micrographs of two regions of a tapered probe showing the rectangular waveguide cavity 610, and an electrical trace 620 connecting from a bond pad 630 to a recording site 650. As discussed supra the probes are formed on a final substrate of ultra-thin silicon which may be of thickness ranging from 10 microns to 100 microns for example. The probes of width potentially of only tens of microns at the tip that may be a hundred millimeters long to provide access to the inner regions of the brain. Such ultra-thin long narrow probes have been shown to be extremely fragile and subject to stress fractures at their midpoint. Accordingly it is desirable in longer probes to reinforce the probe structure.

Figure 7B:
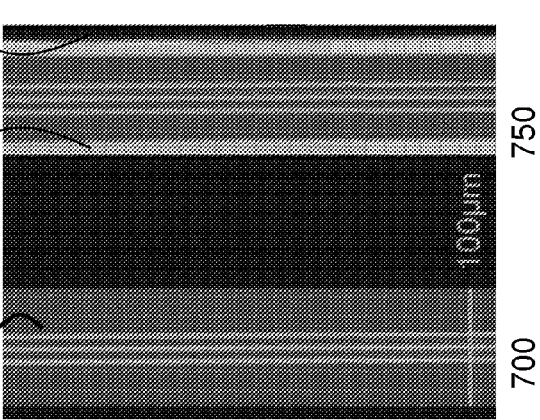
FIG. 7B depicts an optical micrograph of metallization patterns for reinforced and non-reinforced neuronal probes, the former according to an embodiment of the invention.
Figure 7A:
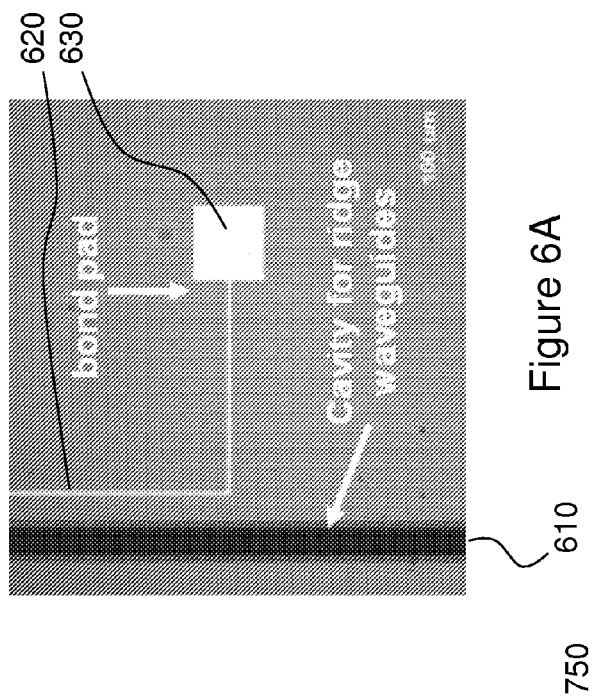
FIG. 7A depicts an optical micrograph of reinforced and non-reinforced neuronal probes, the former according to an embodiment of the invention.

As shown in the optical micrographs of FIG. 7A two ultra-long, thin probes are shown according to the prior art and an embodiment of the invention are shown. The prior art probe 700 being formed without reinforcing structures and having broken approximately at its midpoint, the right portion absent therefore from the optical micrograph. Modified probe 750 in contrast is formed with reinforcing structures and does not suffer stress fractures during processing and release from the substrate as a free standing probe. In FIG. 7B another optical micrograph shows metallization patterns for standard probe 700 and modified probe 750. As shown the standard probe comprises trace metallization 710 between the bond pads and recording sites whilst modified probe 750 features reinforcing metallization 720 either side of the trace metallization 710. These traces being of a predetermined thickness and dimension according to the length, width and thickness of the overall modified probe 750 such that stress along the length of the modified probe 750 is lowered and higher stress regions occur at the head of the probe close to the base carrier region where the dimensions of the silicon probe are increased, thereby increasing the rigidity and mechanical integrity of the ultra-thin silicon probe.

Referring to FIG. 8 there is shown a multiple measurand probe 800 according to an embodiment of the invention wherein electrical stimuli and measurements are made via recording sites 850 which are interconnected to probe pads 870 through electrical traces 860. There are also provided four optical waveguides 880 which address four xerogel based sensing elements 810, being example oxygen sensor 810A, pH sensor 810B, $K^+$ sensor 810C, and $Na^+$ sensor 810D. Alternatively the xerogel based sensing elements 810 may all be sensors for the same measurand, for example oxygen sensors 810A, or other measurands not listed previously. Further the layout of the xerogel based optical sensors 810 and recording sites 850 may be varied according to the requirements of the multiple measurand probe 800, as can the numbers of each of the xerogel based optical sensors 810 and recording sites 850.

Additionally where the optical waveguides 880 are for example silica-on-silicon waveguide structures such as presented supra in respect of probe 500, as opposed to the polymer waveguides within tapered probe 300 which may be incompatible with providing metallization over them due to topographical or material limitations, that the recording sites 850 and electrical traces 860 may be routed and placed with more design freedom as metallization may be provided over the optical waveguides 880 on the upper cladding 540.

POROUS SILICON FOR OPTICAL AND BIOLOGICAL FILTERING: In some instances of deploying these optically based probes it may be appropriate to employ a biological filter within the probe with a controllable pore dimension and porosity. Amongst the different materials that may be considered for such a biological filter is porous silicon which has been shown to range in behaviour between 'bio-inert', 'bioactive' and 'resorbable' by simply varying the porosity of the silicon sample (see for example L. T. Canham in "Bioactive Silicon Structure Through Nano-Etching Techniques", Advanced Materials, 1995, Vol. 7, No. 12, pp. 1033-7). Bioactive porous silicon allows the bonding of body tissues, and within the context of the optically interrogated biosensors according to embodiments of the invention porous silicon has also been reported as forming optical filters, see for example T. Barrett in U.S. Pat. No. 7,177,497 entitled "Porous silicon filter for wavelength multiplexing or de-multiplexing" and I. Rendina et al in "Porous silicon optical transducers offer versatile platforms for biosensors" (SPIE Newsroom Reference 10.1117/2.1200801.0982 http://spie.org/documents/Newsroom/Imported/0982/0982-2008-01-09.pdf), as well as sources through room temperature red-light photoluminescence reported by Canham et al. in "Silicon Quantum Wire Array Fabrication by Electrochemical and Chemical Dissolution of Wafers" (Appl. Phys. Lett. 57, 1046-1048).

Porous silicon thereby offers potential in biological sensing applications that exploit its optical and electrical properties. Single layer or multilayer stacks of porous silicon exhibit a strong modulation of light and can be used in different configurations to behave as optical mirrors, interference filters, rugate filters, and microcavities. The porous multilayer stacks can be designed to match the desired optical behavior, since changes in the reflection and transmission spectra would depend on variations induced in the effective index of refraction which in turn depend on the silicon porosity. At the same time, the high internal surface area of porous silicon material, which can be on the order of several hundred square meters per cubic centimeter of porous silicon, provides an excellent host media to immobilize a wide variety of biomolecules such as DNA, see for example L. De Stefano et al in "DNA Optical Detection Based on Porous Silicon Technology: from Biosensors to Biochips" (Sensors 7, pp. 214-221) and K. L. Beattie et al "Advances in Genosensor Research" (Clin. Chem. 41, 700-706), antibodies such as presented by T. Xue et al in "Research on Immunosensor based on Porous Silicon" (Optoelectronics Letters 4, pp 328-330), antigens such as in O. Meskini et al "Porous Silicon as Functionalized Material for Immunosensor Application" (Talanta 71, pp 1430-1433), and enzymes such as reported by L. A. DeLouise et al in "Quantatitive Assessment of Enzyme Immobilization Capacity in Porous Silicon" (Anal. Chem. 76, pp 6915-6920). These biomolecules being sequestered in the pores of the porous silicon or porous polymer.

The refractive index of the porous silicon material is a weighted average of the refractive indices of the silicon and the pores. As a result of the filling of the pores by these sensor or measurand biomolecules, changes in the refractive index and the optical properties of the porous silicon material occur. These optical variations may be employed as a simple and straightforward transduction approach in optical biosensors. In addition to porous silicon another comparable material of interest are porous polymer photonic bandgap structures. Although porous silicon provides an effective platform for bioactive sensors that extend these sensor concepts into polymeric materials is attractive because of their comparatively simple fabrication processes, cost effectiveness and mechanical flexibility. Recently, nanoporous polymer replicas have been produced from an oxidized porous silicon template for sensing applications, see Y. Y. Li et al in "Polymer Replicas of Photonic Porous Silicon for Sensing and Drug Delivery Applications" (Science, Vol. 299, 2045-2047), and micropatterned polymeric grating structures have been demonstrated as a platform for recognition elements, see R. C. Bailey et al in "Micropatterned Polymeric Gratings as Chemoresponsive Volatile Organic Compound Sensors: Implications for Analyte Detection and Identification via Diffraction Based Sensor Arrays" (Anal. Chem. 75, pp. 2392-2398). Such polymeric materials allow the fabrication of polymer gratings by laser interferometry and extending the number of laser beams allows two-dimensional (2D) and three-dimensional (3D) porous photonic bandgap structures to be fabricated.

Previously in the prior art porous silicon structures have been reported as being prepared through galvano static, chemical, and photochemical etching procedures in the presence of hydrofluoric (HF) acid solutions, see for example H. Foll et al in "Formation and Application of Porous Silicon" (Materials Science & Engineering R-Reports, vol. 39, pp. 93-141), or through stain etching, see for example R. L. Smith et al in "Porous Silicon Formation Mechanisms" (J. Appl. Phys., Vol. 71, pp. R1-R22). Additionally other methods such as pulsed anodic etching, as reported by J. Escorcia-Garcia et al in "Porous Silicon Photonic Devices using Pulsed Anodic Etching of Lightly Doped Silicon" (J. Physics D: Applied, Vol. 42, p. 145101, 7 pp) and by magnetic-field assisted anodization, as reported by T. Nakagawa in "Control of Structure and Optical Anisotropy in Porous Si by Magnetic-Field Assisted Anodization" (Appl. Phys. Letters, Vol. 69, pp. 3206-3208), have also been used for porous silicon preparation.

In these techniques, the pore characteristics such as diameter, geometric shape and direction of the pores not only depend on the composition of the etching solution, but they also depend on temperature, current density, crystal orientation, dopant and doping density of the silicon substrate such as reported by R. L. Smith in "Porous Silicon Formation Mechanisms" (J. Appl. Phys., Vol. 71, pp. R1-R22). In addition to all of these material factors affecting formation of the pores all of these techniques are harsh etching methods that require a hard mask of silicon nitride, metals or silicon oxide to shield other areas of the sensors/devices against etching.

POROUS SILICON FABRICATION: It would be beneficial if a dry etching technique was available that was compatible with ultra-thin silicon substrates, for biosensors in intrusive applications such as brain and organ measurements, and with semiconductor processing for compatibility with high volume, low cost manufacturing. The inventors have identified that xenon fluoride (XeF2) may be employed to form porous silicon structures. Accordingly, the inventors have established a plasma-less etching technique using XeF2 which is based on the reaction of the fluorine ions, which represents the main etchant, with the solid silicon to produce the volatile gas silicon fluoride (SiF4) at room temperature. In this processing undissociated gaseous XeF2 is absorbed onto the exposed areas of bulk silicon wherein the adsorbed gas is then dissociated into xenon and fluorine. The resultant fluorine ions react with silicon to produce SiF4, which disassociates into the gas phase at room temperature and leaves behind a porous silicon surface. The chemical reaction for the etching of silicon by XeF2 is given by equation (1) below:

$$Si + 2XeF_2 \rightarrow SiF_4 + 2Xe \quad (1)$$

In addition to its etching process simplicity, XeF2 has a high etch selectivity to silicon which allows a standard hard baked layer of photoresist to serve as the masking layer. Whilst XeF2 reacts readily with silicon, it is relatively inert to photoresist, silicon dioxide, silicon nitride and aluminum, which further allows this technique to be used in the presence of CMOS integrated circuits thereby allowing the formation of porous silicon to be a post processing step.

The inventors have fabricated two types of porous silicon samples, porous silicon on bulk silicon for sensing platforms and ultra-thin porous silicon membranes for biological sample filtering. The silicon wafers used for fabricating porous silicon on bulk silicon were 3 inch diameter, 381±20 µm thick, <100> orientation, and boron-doped (5-10 ohm-cm). A 1.4 µm thick layer of photoresist was spin coated and photolithographically patterned to provide the apertures within which the porous silicon was to be formed. Because of the high selectivity of the XeF2 etch technique, the silicon samples were dipped in a diluted H2O:HF solution (10:1) for approximately 3 seconds to remove native oxide which would otherwise prevent the XeF2 from etching the silicon underneath. The samples were then dried with flow of nitrogen and immediately loaded in the etching chamber of the XeF2 system. The XeF2 system uses a source bottle of XeF2 which is a dense white crystalline solid with a room temperature vapour pressure of roughly 4 Torr and is connected to the etching chamber via a vacuum pump and expansion chamber.

The etching process begins with placing the etching chamber under vacuum after which XeF2 flows into the expansion chamber and into the etching chamber, wherein etching begins when the pressure reaches $3 \times 10^{-2}$ mbar. This vacuum—expansion—etch cycle is repeated and the etched thickness depends on the number of cycles executed. Before and after each etching process, the complete vacuum system was purged with nitrogen many times to remove any residual gases. The hard-baked photoresist layer is then removed using an oxygen plasma system in which reactive species combine with the photoresist to form ash which is removed under vacuum. The native oxide present on the other side of the silicon wafer prevents the XeF2 etching the silicon underneath during the etching process. It would be evident to one skilled in the art that this dry etching process removes the requirement for a drying step which is critical in wet etching processes and which is a significant yield reducing step when considering thin membranes of a micron or so in thickness. High porosity and/or porous layer thickness leads to a systematic cracking of the layer during the drying process of wet etching as the solvent evaporates. This arises due to large capillary stresses occurring during evaporation as a pressure drop occurs across the gas/liquid interface within the pores.

Figure 9C:
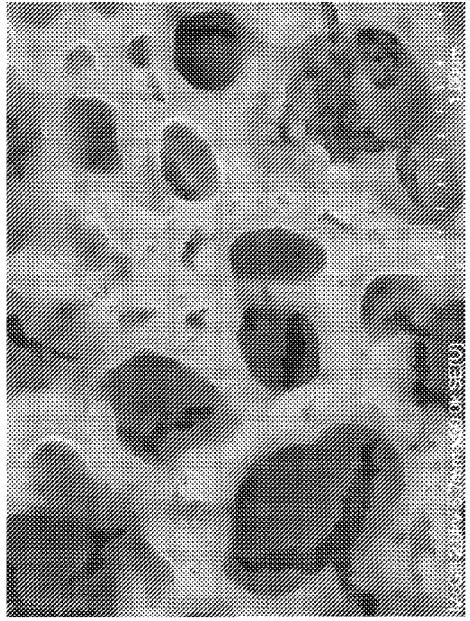
FIGS. 9A through 9H depicts exemplary porous silicon according to an embodiment of the invention at various magnifications and etch depths through SEM micrographs.
Figure 9D:
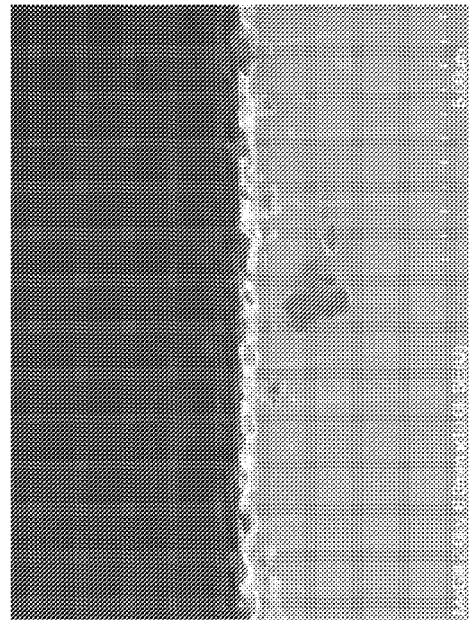
Figure 9A:
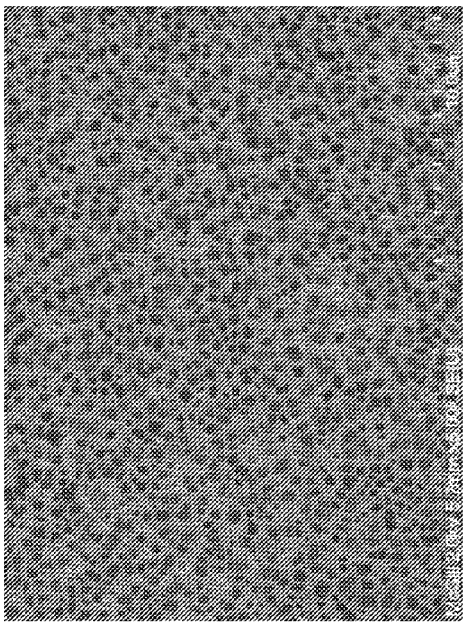
Figure 9B:
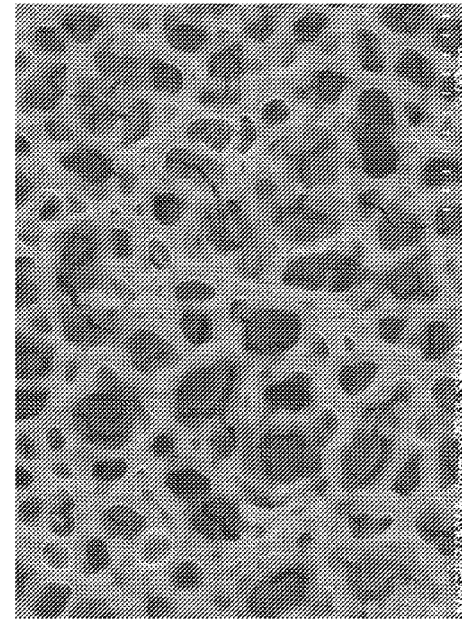
Figure 9F:
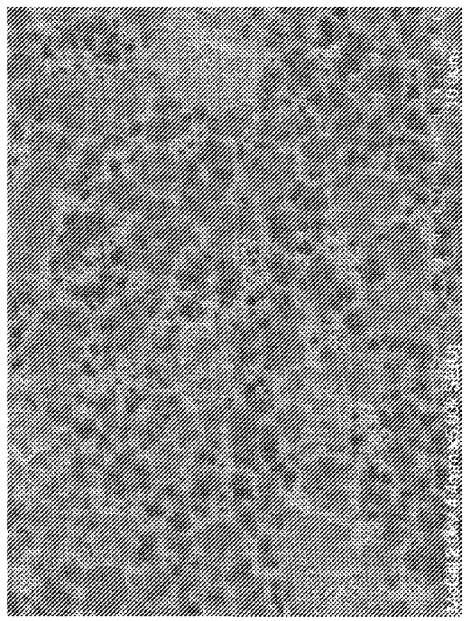
Figure 9H:
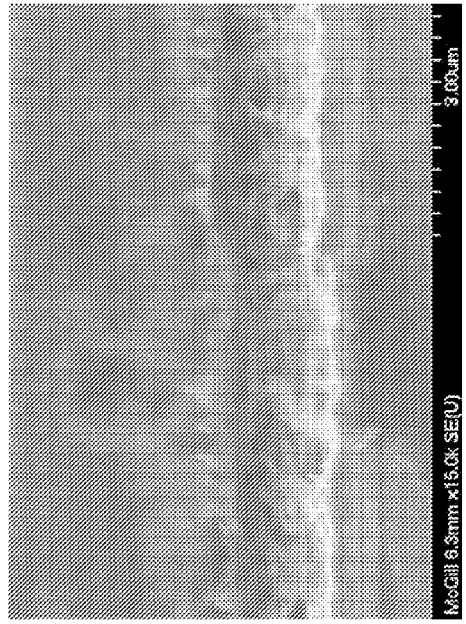
Figure 9E:
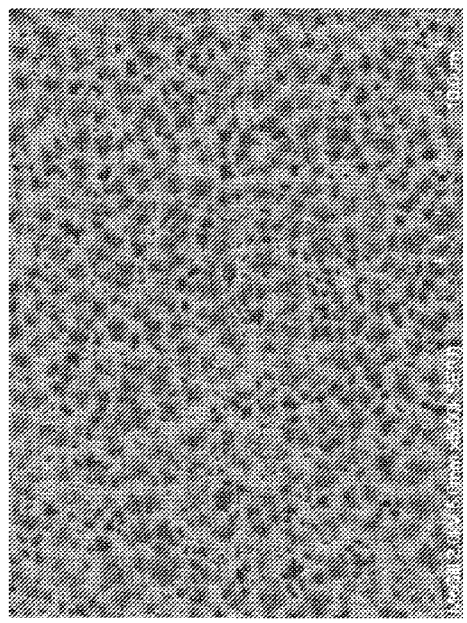
Figure 9G:
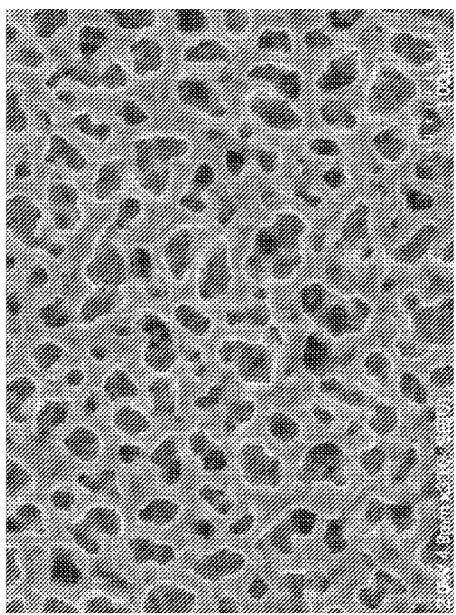

Referring to FIGS. 9A through 9D SEM micrographs of a 10 µm deep etch are presented. In FIGS. 9A through 9C the porous silicon surface is imaged at increasing magnifications for regions approximately 25 µm square, 5 µm square and 2.5 µm square respectively. FIG. 9D presents a cross-section of the bulk silicon after etching showing the porous silicon at the surface, wherein the thickness of the porous silicon layer is approximately 571±96 nm Referring to FIGS. 9E and 9F the porous silicon layers from the 20 µm and 30 µm etching processes are shown in these SEM micrographs at the same magnification as FIG. 9A. FIG. 9G presents the porous silicon at increased magnification for the 20 µm etching whilst FIG. 9H shows the porous silicon in cross-section at high magnification for the same 20 µm etching.

In the cross-section SEM micrographs the bottom surface of the pores for the 10 µm etched sample (FIG. 9D) is flat and has few cracks. These cracks will open up if further etching was performed and for the 20 µm etched sample, cracks on the bottom surface are wider and new pores are formed. For the 30 µm etched sample (FIG. 9F), the surface of the material becomes very irregular, no obvious layered structure is observed and only scattered web formations are noticed in the cross-sections (not presented within the figures).

Now referring to FIGS. 10A through 10C there is shown an exemplary process according to an embodiment of the invention for forming a porous silicon membrane (filter). In FIGS. 10A and 10B a porous silicon filter 1000 formed through a two-step dry etching process is shown wherein a hard baked photoresist layer has been used to form a masking layer to leave surround 1040, the resulting porous silicon filter 1000 comprising membrane 1010 with pores 1020. The dual-stage process is shown in FIG. 10C wherein a silicon wafer 1060 has photoresist 1050 coated on both sides. The process then consists of patterning the front and back surfaces to provide the openings within the photoresist 1050. The first XeF2 etching forms recess 1070 at the bottom of which is porous silicon on the silicon wafer 1060. The second X2F2 etching results in the thin membrane 1080 of porous silicon. Finally removal of the photoresist results in the free-standing thin membrane 1080 within the silicon wafer 1060.

To form ultra-thin porous silicon films for biological sample filtering, 50 µm thick, 4" diameter double side polished silicon wafers were used. As with the bulk silicon processing a 1.4 µm thick layer of photoresist was spin coated and photolithographically patterned to expose the windows for etching. The silicon sample was then flipped over and the same process is repeated to create a cross-sectional aligned and photolithographically patterned (exposed) on the other side. The silicon samples were similarly dipped in a diluted H2O:HF solution for native oxide removal. The sample was then etched using XeF2 with a 10 µm etch depth into the bulk silicon substrate on one side before the sample is flipped and the sample was again etched, using XeF2, 38 µm deep into the bulk silicon substrate on the other side. This created an ultra-thin porous silicon membrane of 1.2 µm thick but cross-sectional SEM images were difficult to obtain. However, optical characterization was performed giving the thickness of the porous silicon membrane as on the order of 1 µm.

Figure 10D:
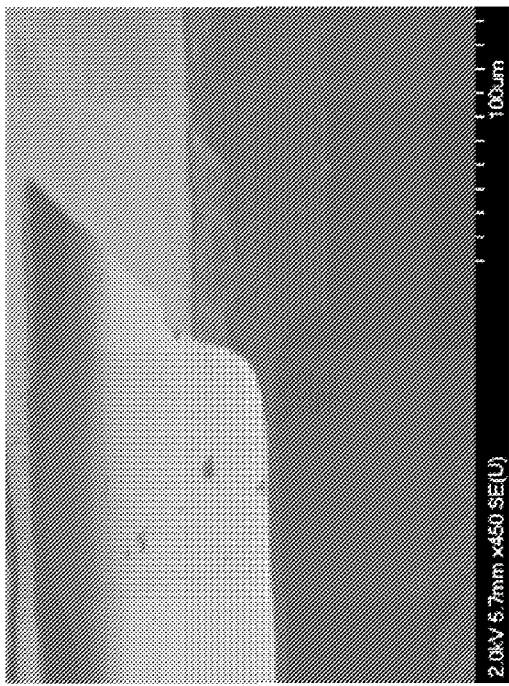
FIGS. 10D and 10E depict SEM micrographs of a porous silicon membrane formed according to an embodiment of the invention.
Figure 10E:
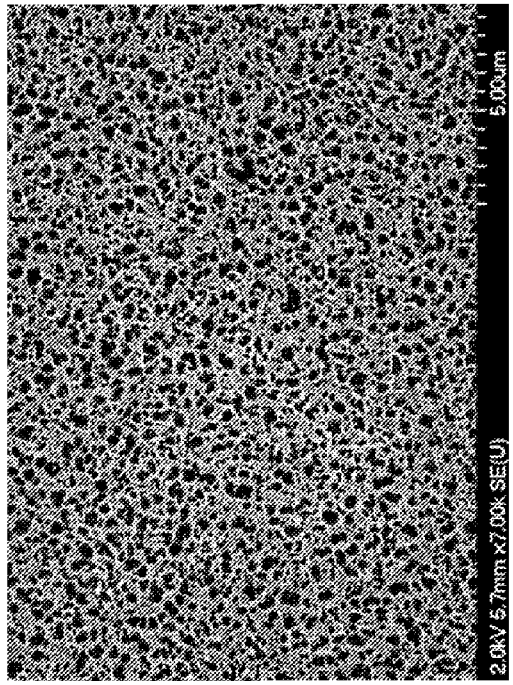
Figure 11:
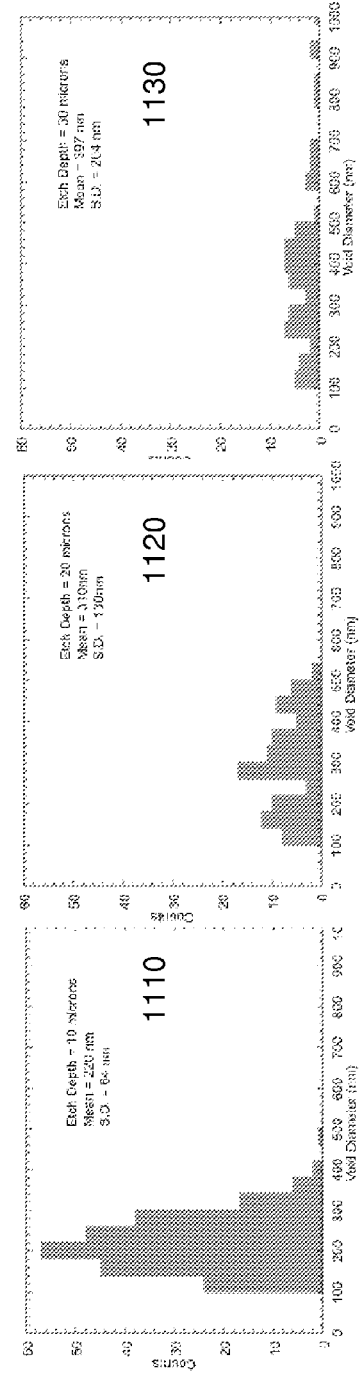
FIG. 11 presents pore dimension distributions for porous silicon structures fabricated according to an embodiment of the invention for varying etch depth.

Referring to FIG. 10D there is shown a cross-section SEM of a 5 µm thick porous silicon membrane, whilst FIG. 10E shows a SEM micrograph of one side of the porous membrane. Now referring to FIG. 11 there are shown first through third histogram distributions 1110 through 1130 respectively which relate to measurements performed on samples from the 10 µm, 20 µm and 30 µm etch processes respectively. These depict average pore diameters of 220 nm, 310 nm, and 397 nm respectively. Over this 20 um range the average pore diameter increases with etch depth at approximately 88.5 Å/um.

Figure 12A:
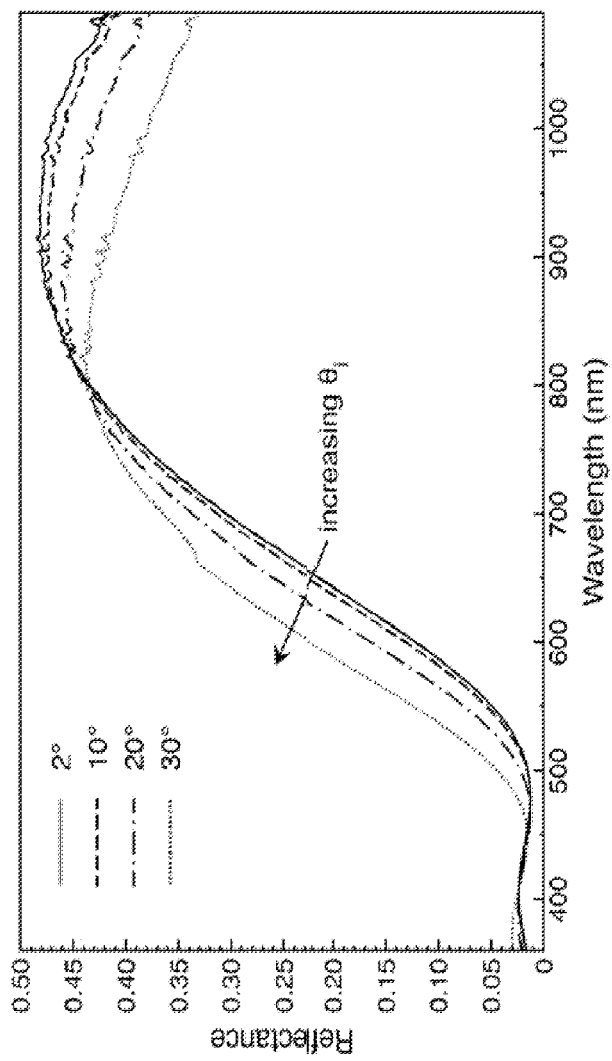
FIGS. 12A and 12B depict the angular dependence of the optical reflectance of a 10 μm etched porous silicon sample according to an embodiment of the invention.

OPTICAL CHARACTERIZATION OF POROUS SILICON: Reflectance of the optical interference properties of the porous silicon material for porous silicon fabricated according to an embodiment of the invention was measured between 350 nm and 1100 nm as shown in FIG. 12A using a Xenon arc lamp in conjunction with a monochromator. The reflectance was measured at 2°, 10°, 20°, and 30° angles of incidence for the source to the porous silicon with the photodetector placed parallel to the porous silicon surface for a 10 µm etched bulk porous silicon sample. A low angle of incidence, there is a reflectance minimum near 500 nm which as the angle of incidence increases shifts to shorter wavelengths. This behaviour strongly indicates the porous silicon layer is acting as a Fabry-Perot structure and that the observed reflectance minimum is the result of destructive interference between the porous silicon/air interface and the bulk silicon/porous silicon interface.

FIG. 12A demonstrates the ability of porous silicon to behave as an optical interference filter by reflecting a particular wavelength range thus allowing selective enhancement of the wavelengths of interest, in other words, it is possible to reduce the reflection of the excitation signal, while enhancing the backscattering detection of the luminescence signal within luminescent sensor devices. As will be shown below in respect of FIGS. 15 and 16 the 10 µm etched porous silicon sample is particularly suitable to provide optical filtering for an optical oxygen sensor based on absorption/emission of the tris(bipyridine)ruthenium(II) ([Ru(bpy)$_2$]$^{2+}$) luminophore for which the typical excitation wavelength is around 470 nm, while its luminescence peak is at 610 nm, see R. Narayanaswamy et al in "Optical Sensors: Industrial, Environmental and Diagnostic Applications" (Springer, New York, 2004).

Figure 12B:
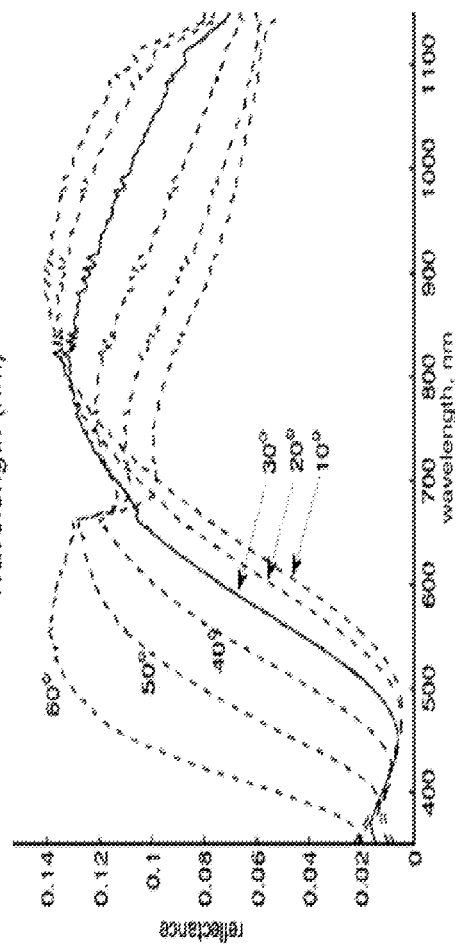

Referring to FIG. 12B optical reflectance measurements between 350 and 1100 nm are shown at 10°, 20°, 30°, 40°, 50° and 60° angles of incidence for the 10 µm porous silicon sample. Whilst the shift to lower wavelength continues at increasing incidence another feature of interest appears, namely the abrupt change in the reflectance around 660 nm for angle of incidence above 30°. This feature is most likely a polarisation effect where the angle of reflectance for porous/bulk interface is beyond the Brewster Angle for wavelength above 660 nm. Although these optical reflection measurements alone cannot provide a conclusive estimate on the refractive index or the porous layer thickness of these samples, it can be concluded from measurements on different etch depths that the more the silicon is etched, the greater is the optical thickness. Moreover, the increase in the porosity usually lowers the effective refractive index of the porous material, see D. Riley et al in "Effect of Porosity on the Optical Properties of Anodized Porous Silicon Thin Films" (Annual Report Conf. on Electrical Insulation and Dielectric Phenomena, 1998, vol. 1, pp. 248-251), giving the expectation for reducing optical thickness with increased etching, but this is not the case. Therefore the thickness of the porous layer, that is the distance between the top surface of the web of nanocrystals and the surface underlying the top surface, must be larger with the increase in etching depth. This phenomenon holds good till the top surface of the porous silicon can maintain its structure with the continued etching process.

Figure 13:
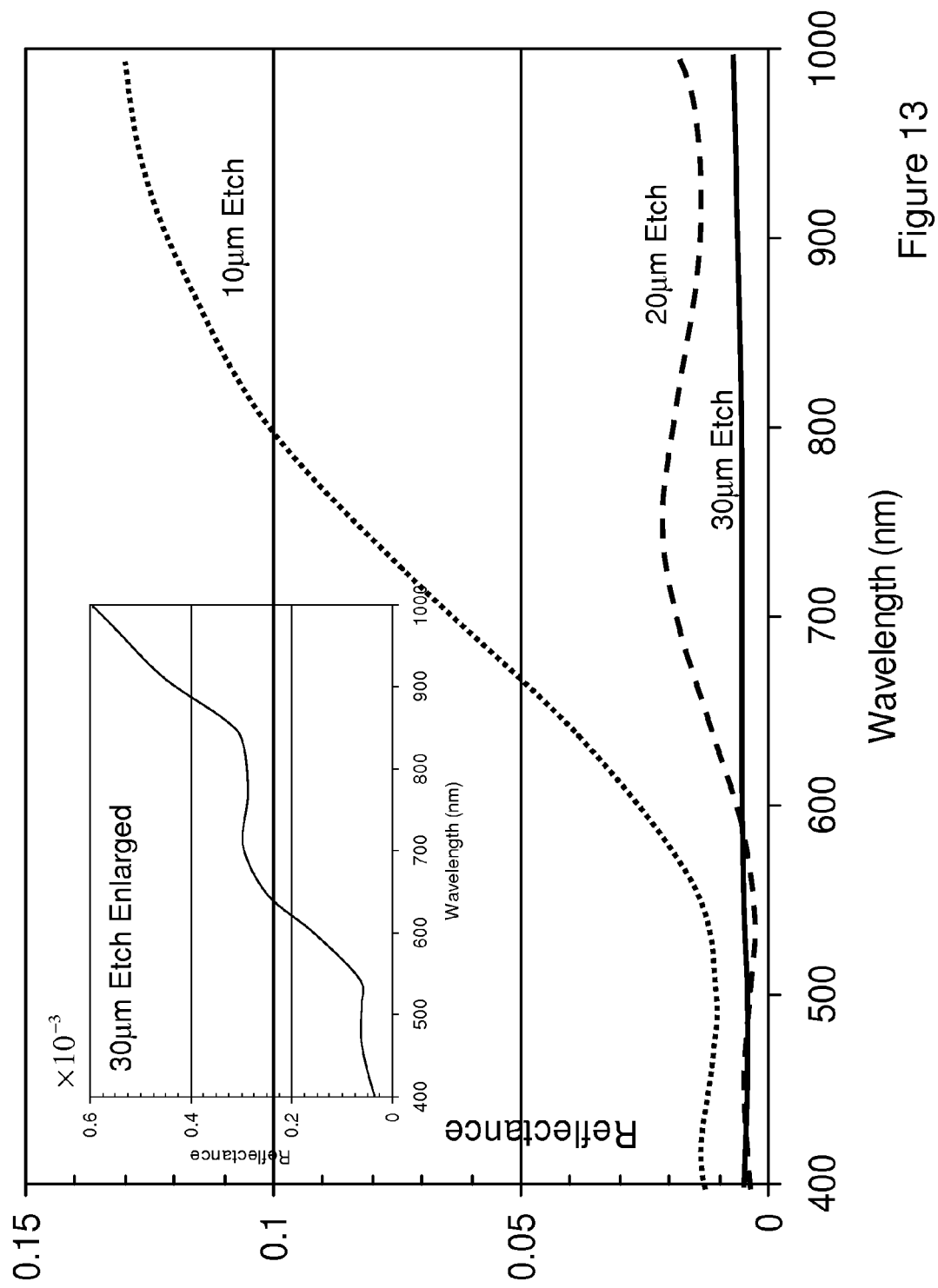
FIG. 13 depicts the angular dependence of the optical reflectance of a porous silicon sample according to an embodiment of the invention as a function of etch depth.

Referring to FIG. 13 there is shown the reflectance spectra for 10 µm, 20 µm, and 30 µm etch samples at 2° incidence. As is evident from FIG. 13 the reflectance spectra reduce in magnitude with increasing etch depth, such that for the 30 µm sample the reflectance is dramatically reduced and is constantly below 1%. The reflectance of the three porous silicon samples contain many undulations or fringes, and the fringe density increases with deeper etching. These fringes in the reflectance are the result of the interference between the reflected light from the web like top surface of the porous silicon and the reflected light from the porous/bulk interface. Effectively, if we treat the layer of porous silicon as a Fabry-Perot oscillator, then the condition for destructive interference is given by equation (2) below:

$$2nd = \left(m - \frac{1}{2}\right)\lambda \qquad (2)$$

where n is the refractive index, d is the porous layer thickness, m is the spectral order of the optical mode and λ is the wavelength. When comparing the fringe pattern in these measurements with the spectral minima indicated by Equation (2), it is found that the thickness of the porous silicon is on the order of λ/n, where λ is in the visible and near visible region.

Specifically, using Equation (2) it is possible to deduce the optical thickness (nd) for the 20 µm sample to be approximately 690 nm, with the minimum for m=2 around 930 nm and the minimum for m=3 around 550 nm. Although SEM analysis showed no obvious layered structure for the 30 µm sample features from optical interference can still be observed in its reflectance, as shown in the inset of FIG. 13. These features, specifically the minima at 580 nm and 820 nm, indicate that the optical thickness of the porous material for this etch depth is approximately 1.0 µm (m=3 around 820 nm, m=4 around 580 nm). Finally, for the 10 µm etching the optical thickness of the porous layer is around 380 nm (m=1 around 1500 nm, m ¼ 2 around 500 nm), but an optical thickness of 125 nm (m=1 around 500 nm) is also possible such that more information is needed to verify the optical thickness of this etch depth.

Figure 14:
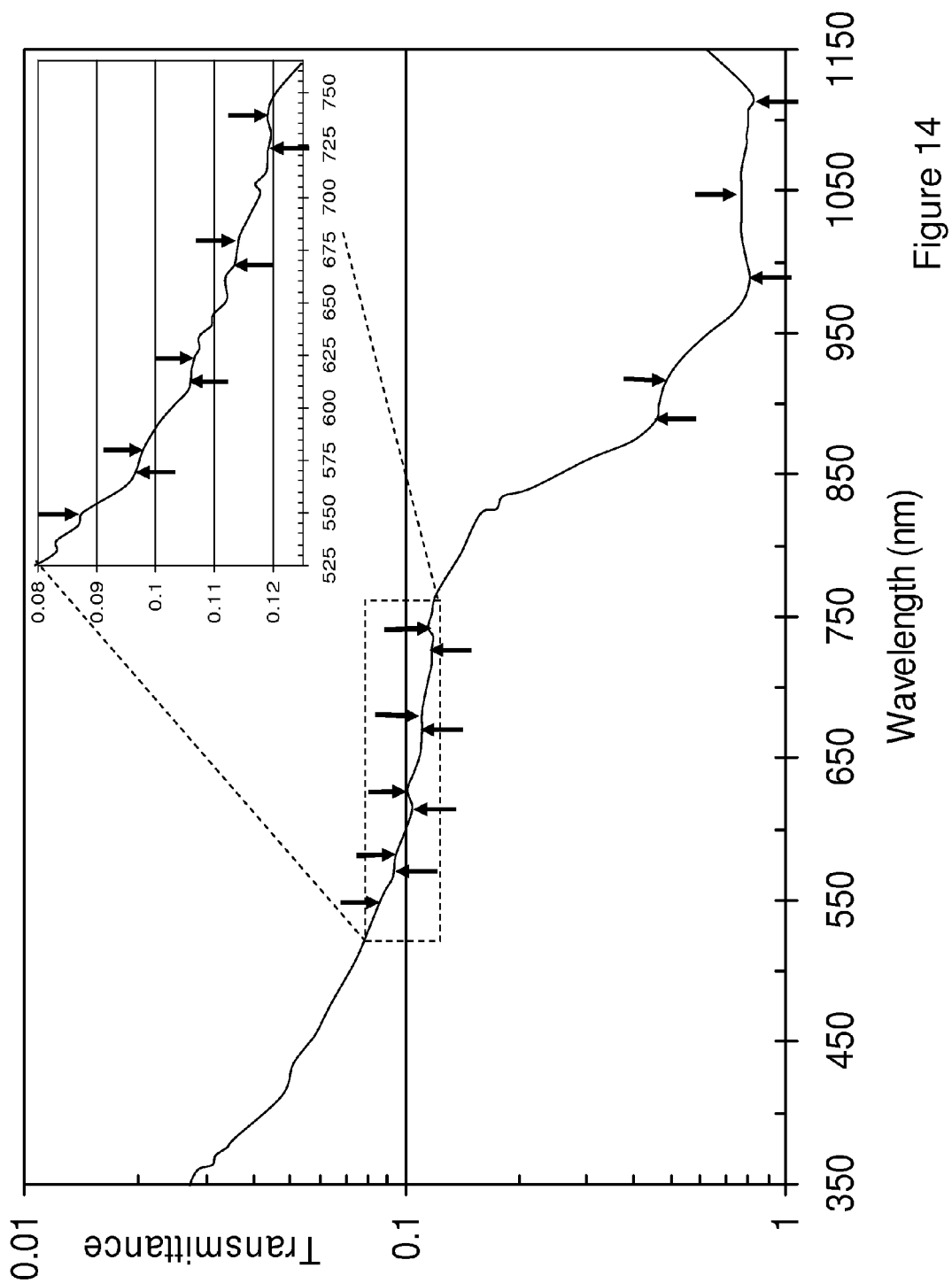
FIG. 14 depicts the optical transmittance of a free-standing porous silicon membrane according to an embodiment of the invention.

Referring to FIG. 14 there is shown the optical transmittance spectra for an ultra-thin (fabricated thickness on the order of 1 µm) free-standing porous silicon membrane. The porous silicon membrane has a typical transmission spectrum of silicon modulated by Fabry-Perot fringes. These fringes, indicated on the inverse-logarithmic plot of transmittance by arrows, show that the porous membrane is on the order of a micron in thickness which is in good agreement with the expectation based upon starting wafer thickness, etch rate, and processing time. As evident from FIG. 14 the porous silicon can pass above 10% light visible wavelengths longer than approximately 600 nm, and has very good transmittance in the near infra-red beyond 900 nm and reaches approximately 75% in the 1000-110 nm region.

POROUS POLYMER FABRICATION: As noted supra porous polymer photonic bandgap structures offer an extension to porous silicon through their comparatively easy fabrication process, cost effectiveness and mechanical flexibility. Amongst such structures are micropatterned polymeric gratings that have been demonstrated both as a platform for recognition elements, see for example R. C. Bailey at al in "Micropatterned Polymeric Gratings as Chemoresponsive Volatile Organic Compound Sensors: Implications for Analyte Detection and Identification via Diffraction-Based Sensor Arrays" (Anal. Chem. 75, pp 2392-2398), and as diffractive fixed and tunable Bragg gratings. In order to form porous polymer photonic bandgap structure according to one applicable manufacturing methodology, namely photo-polymerization which is a low temperature process providing compatibility with CMOS electronics, planarization materials etc, a pre-polymer mixture comprising a monomer, photoinitiator, and different solvents is provided from which the porous polymer will be formed.

An exemplary pre-polymer mixture may comprise an acrylate monomer (e.g. dipentaerythritol penta-hexa-acrylate (DPHPA)), coinitiator (e.g. NPhenylglycine (NPG)), photoinitiator (e.g. 4,5,6,7-tetrachloro-2',4',5',7'-tetraiodofluorescein, commonly known as Rose Bengal (RB)), reactive solvent (e.g. 1-Vinyl-2-pyrrolidone (NVP)), and a surfactant (e.g. dioctyl sodium sulfosuccinate, also known as docusate sodium salt (DSS). The reactive solvent, NVP, reduces the viscosity of the monomer whilst also improving the homogeneity of the pre-polymer mixture. Further, NVP also aids in dissolving the photoinitiator and co-initiator, as well as being part of the chemical reaction in the formation of the cross-linked polymeric structure. Finally, these chemicals are dissolved in a nonreactive solvent, formamide, for processing.

Accordingly a pre-polymer mixture employed in fabricating porous polymer structures is 1 wt % NPG, 0.5 wt % RB, NVP 25 wt %, AOT 6.5 wt %, DPHPA 42 wt %, and formamide 25 wt %. One of the advantages of this pre-polymer syrup is that it can contain recognition elements for chemical and biological sensing. For example, using porous gratings (a 1D photonic bandgap structure) a prototype oxygen sensor may be implemented using tris(4,7'-diphenyl-1-10'-phenanthroline) ruthenium(II) chloride pentahydrate ([Ru(dpp)$_3$] Cl$_2$.5H$_2$O) and ethanol as oxygen recognition elements. These may be added and mixed to the previously prepared pre-polymer mixture with a 1:4 ratio, for example.

Photo-polymerization may employ flood illumination for forming bulk porous polymers or exploit conventional optical laser interference between multiple beams to provide a porous polymer with an embedded Bragg diffraction grating structure. The laser for example being a solid state diode pumped laser operating at 532 nm. The pre-polymer mixture when exposed to the optical laser illumination undergoes photo-polymerization, this process being higher in the bright constructive interference regions and lower in the dark destructive interference regions of the interference pattern. This results in a periodic structure due to the phase separation of the two different chemicals in the pre-polymer syrup under polymerization. The grating spacing can be calculated according to the Bragg condition as given by Equation 3 below. To ensure complete polymerization during production a post-curing process with flood UV exposure may be added.

$$\Lambda = \frac{\lambda_{bragg}}{2n_{ave}\sin\theta} \quad (3)$$

where, $\Lambda$ is the grating spacing, $n_{ave}$ is the average refractive index of the grating film, $\lambda_{bragg}$ is the reflected wavelength, and $$\theta = \sin^{-1}\left\{\left(\frac{n_{prism}}{n_{sample}}\right) \times \sin\left[\left(\frac{\pi}{4}\right) - \sin^{-1}\left(\sin\frac{\Phi}{n_{prism}}\right)\right]\right\} \quad (4)$$

It would be evident to one skilled in the art that the reflection spectrum of the grating can be tuned by changing the geometry of the optical interference system generating the grating during the fabrication process. This optical property provides the ability to tune the characteristic response of the reflection grating depending upon the absorption/emission spectrum of the recognition elements, e.g. luminophores, for a particular sensor element. In addition to the controllable reflection characteristics from fabrication parameter adjustment, the reflection spectrum can be tuned by changing the optical geometry of grating, i.e. the reflection wavelength can be tuned by changing the angle of incident beam. This is a significant advantage of the porous polymer bandgap structure as this post-fabrication tuning provides more flexibility in designing sensors and selecting sensor materials. It would be evident that in this manner a direct write optical laser interference photo-polymerization process may be employed to establish each sensor within an array of sensors with the correct grating characteristics. Further exploiting the robotic localized dispensing methodology outlined supra in respect of FIGS. 1 and 3 it would be evident that the pre-polymer mixture may be dispensed into each sensor location individually allowing localized variation in the recognition material. Amongst the classes of materials that may employed within the pre-polymer mixture for the recognition material are "porogens". Porogens are substances that are soluble in the monomers from which a polymer is formed, but insoluble within the as formed polymers. Thus, as polymerization proceeds, the pores are formed in the spaces where porogens are found.

With these porous nano structures the optical properties of the grating are not degraded by functional enhancement of the pre-polymer mixture by the inclusion of additional materials such as the oxygen recognition element [Ru(dpp)$_3$]$^{2+}$. These additional materials are positioned within the polymer structure as their molecular size is smaller than both that of the polymer chains and that of the voids within the grating structure. It would be evident to one skilled in the art that such porous polymers may be employed in conjunction with porous silicon structures. For example a porous silicon biological filter may be employed in conjunction with a porous polymer grating structure that provides optical filtering for the optically interrogated sensor element.

Such a dual porous material probe being shown by probe 1500 in FIG. 15. As shown probe 1500 comprises a micro-machined silicon structure 1520 upon which a metallization structure has been formed of which only the bond pad 1550 and recording site 1545 are visible at the upper surface of the upper planarization/passivation layer 1510, which may be for example Parylene™ C 190 as presented supra in respect of FIGS. 1A through 1I. Also formed within the upper planarization/passivation layer 1510 is sensor access 1580 which is an opening down to the sensor element within the probe 1500. One the lower side of the micro-machined silicon structure 1520 is lower planarization/passivation layer 1530. Also shown is channel waveguide 1540 that is similarly formed in the lower surface of the micro-machined silicon structure 1520 and provides the optical interconnect to the sensor structure within the probe 1500.

Also shown in FIG. 15 is cross-section X-Y-Z which is formed from first section X-Y along the rear area of the probe 1500 and second section Y-Z along the length of the probe 1500. Considering first section X-Y then at the bottom is lower planarization/passivation layer 1530 on top of which is micro-machined silicon structure 1520 that is full thickness from the edge X of the section until it reaches the central portion of the probe 1500 wherein the channel waveguide 1540 is formed within the lower surface of the micro-machined silicon structure 1520. On the upper surface of the micro-machined silicon structure 1520 is deposited the upper planarization/passivation layer 1530 which overlays the interconnection metallization 1555 between the bond pad 1550 and recording site 1545 as well as the micro-machined silicon structure 1520. Deposited below the interconnection metallization 1555 and bond pad 1550 is adhesion layer 1560, for example the 20 nm thin layer of titanium described supra in respect of FIG. 1B.

Now considering the second section Y-Z which is along the length of the probe 1500 then for the majority of this length the cross-section consists of upper planarization/passivation layer 1530, micro-machined silicon structure 1520 within which is formed channel waveguide 1540, and lower planarization/passivation layer 1510. However, at the tip of the probe 1550 there is formed the optical sensor structure. Within this region the micro-machined silicon 1520 has been processed by XeF2 etching to form porous silicon biological filter 1570. Above the upper surface of the porous silicon biological filter 1570 is sensor access 1580, whilst beneath it is porous polymer biological reactant 1590 which was deposited and polymerized in accordance with embodiments of the invention described supra. As such porous polymer biological reactant 1590 may be a bulk porous polymer sensor or one employing a Bragg grating structure to provide enhanced sensitivity for the optically interrogated sensor.

INTEGRATED OPTO-ELECTRONIC PROBES EMPLOYING OPTICAL INTERROGATION AND POROUS SILICON: Luminescence based sensors are widely used in medical and biomedical applications, see for example C. McDonagh in "Optical Chemical Sensors" (Chem. Rev. 108, pp. 400-422) and R. Narayanaswamy in "Optical Sensors: Industrial, Environmental and Diagnostic Applications" (Springer, New York). Luminescence based biosensors offer a number of advantages including high sensitivity and selectivity, fast response times, easy implementation, and stand-off detection. As outlined supra a wide variety of porous silicon based biosensors can be implemented that exploit its optical properties and its ability to host a broad range of biomolecules to sense for example antigens, DNA, proteins, toxins, viruses, and immunoglobulin G (IgG) molecules.

As described supra XeF2 dry etching of silicon allows the selective formation of porous silicon where a standard hard baked photoresist layer can serve as a masking layer and coupled with low temperature processing allow compatibility with post-processing integrated CMOS electronic wafers. Further the pore size, morphology, and thickness of the fabricated porous silicon layer can be easily controlled in the etching process. In the description that follows in respect of FIGS. 16 and 17 the inventors have employed a porous silicon platform to develop an optical filter-less sensor based on encapsulating the oxygen responsive luminophore, tris(2,2'-bipyridyl) dichlororuthenium(II)hexahydrate ($[Ru(bpy)_3]^{2+}$·$6H_2O$) in sol-gel derived xerogel thin-films with these materials being deposited on top of porous silicon substrate.

This configuration as discussed supra allows for selective enhancement of the detection efficiency for the selected wavelengths of interest. Similarly, the inventors have demonstrated the ability of porous photonic bandgap structures to sense volatile organic compounds (VOCs) such as acetone, methanol, pyridine, and toluene. These sensors operate on the principle of colorimetric measurements when the VOC vapors penetrate into the voids in the grating structures, see for example X. Y. Fang et al in "Colorimetric Porous Photonic Bandgap Sensors with Integrated CMOS Color Detectors" (IEEE Sensors J., Vol. 6, pp 661-667) and V. K. S. Hsiao et al in "Optical Microfabrication of Highly Reflective Volume Bragg Gratings" (Appl. Phys. Lett., Vol. 86). Unfortunately, those gratings provide limited selectivity and hence, there is a need to develop the porous structures according to embodiments of the invention as a universal template for chemical and biological sensors.

Exploiting the structures within the embodiments described supra in respect of FIGS. 9 through 14 allows us to significantly enhance the selectivity of these reflection grating structures with the development of a generic template for the encapsulation of recognition elements to sense a variety of analytes such as biochemicals, toxins, pollutants, and biomarkers.

POROUS SILICON SENSOR FABRICATION: The preparation of a xerogel based oxygen (O2) sensor according to an embodiment of the invention for which the results are presented in FIGS. 16 and 17 outlined below. The xerogel was prepared by acid catalyzed hydrolysis and polycondensation of 3-methacryloxypropyltrimethoxysilane (MAPTMS) in combination with methacrylic acid and zirconium oxide (ZrO2). Accordingly, 10.14 g (0.040 mol) MAPTMS was combined with 0.54 g of 0.05M hydrochloric acid (HCl). The solution was stirred and aged for 1 hour at room temperature. During this time, a separate solution was prepared from 6 g (0.013 mol) of 70% zirconium(IV)propoxide in 1-propanol and 1.1 g (0.013 mol) of methacrylic acid. These were combined and aged for 40 minutes. The MAPTMS solution is added drop-wise to the zirconium solution. The resulting xerogel is further hydrolyzed by the addition of 0.98 g distilled water and stirred while being aged for at least 16 hours. The final ratio of water to silicon (r value) is 1.5. The luminescence sensor was prepared from a 1:4 mixture of 10 mmol/L tris(2,2'-bipyridyl) dichlororuthenium(II)hexahydrate in water and MAPTMS sol. 400 µL aliquots of ($[Ru(bpy)_3]^{2+}$·$6H_2O$) were added to 1400 µL MAPTMS sol. Rapid gel formation was avoided by adding 1 mL of methanol containing 200 µL water to the final sol. The xerogels sensors were spin coated onto the porous silicon platform forming a 2 µm thick layer. The samples were then aged for 5 days before experimental testing.

Figure 16:
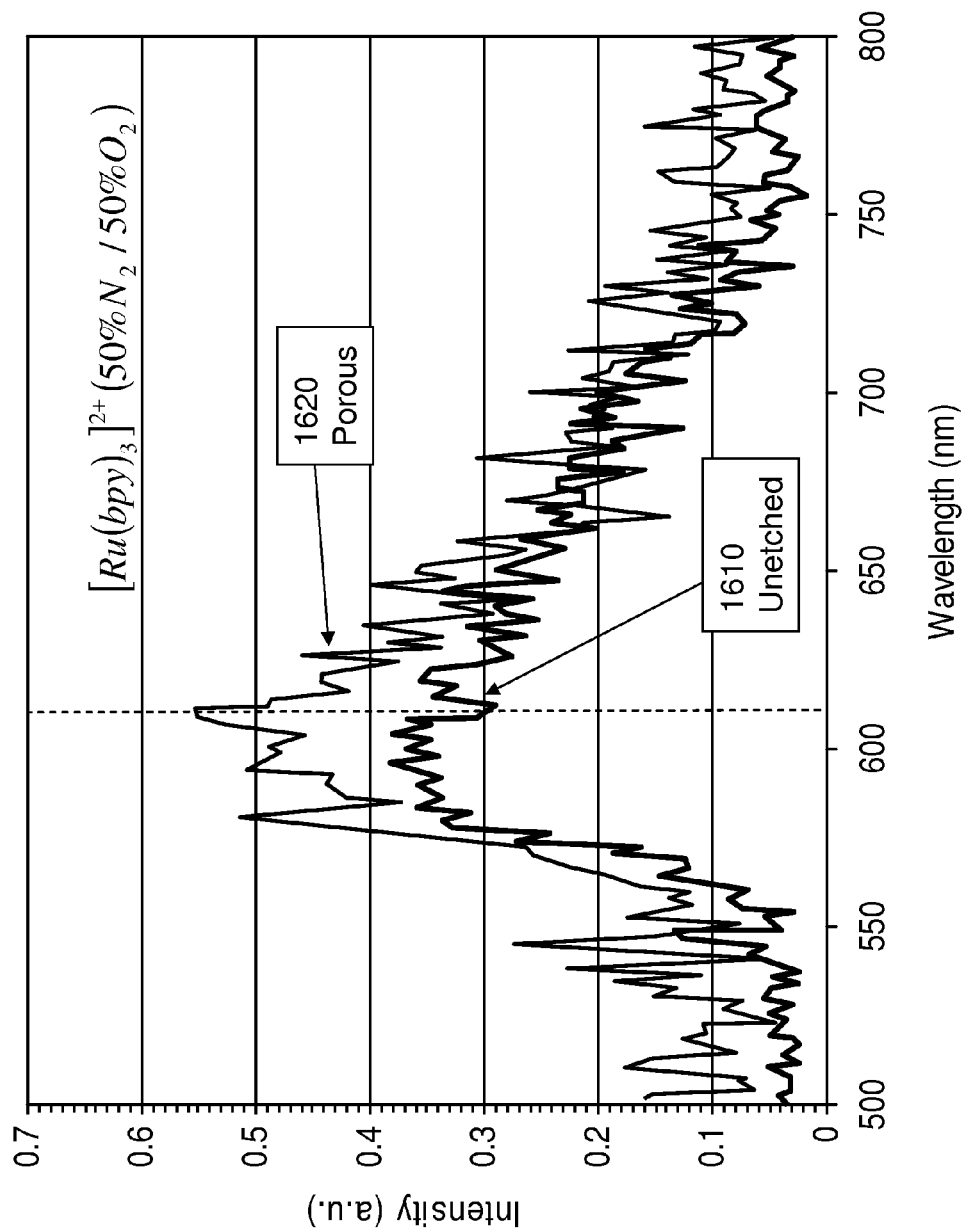
FIGS. 16 and 17 depict the performance of an optical oxygen sensor formed according to an embodiment of the invention employing porous silicon.

POROUS SILICON OXYGEN SENSOR RESULTS: Xerogels are ideally optically transparent materials and hence, in an integrated device with xerogels coated on top of a porous silicon substrate, the porous silicon plays the role of a reflection type Fabry-Perot interference filter. From FIG. 12A it was evident that an angle of incidence of 30°, the porous silicon substrate is particularly suitable to provide optical filtering for an optical oxygen sensor based on the xerogel matrix embedded with the $[Ru(bpy)_3]^{2+}$ luminophore. The typical excitation wavelength of this luminophore is around 470 nm, while its luminescence peak is at 610 nm. Therefore, using the porous silicon as substrate for the xerogel matrix would reduce the reflection of the excitation, while enhancing the backscattering detection of the luminescence. FIG. 16 shows spectrograph results for sensor devices fabricated using an unpolished (rough) silicon wafer substrate, first response curve 1610 with intensity of approximately 0.36, and porous silicon substrate, second response curve 1620 with intensity approximately 0.53. The porous silicon representing in this initial prototype an improvement of approximately 50% for the oxygen sensor.

Figure 17:
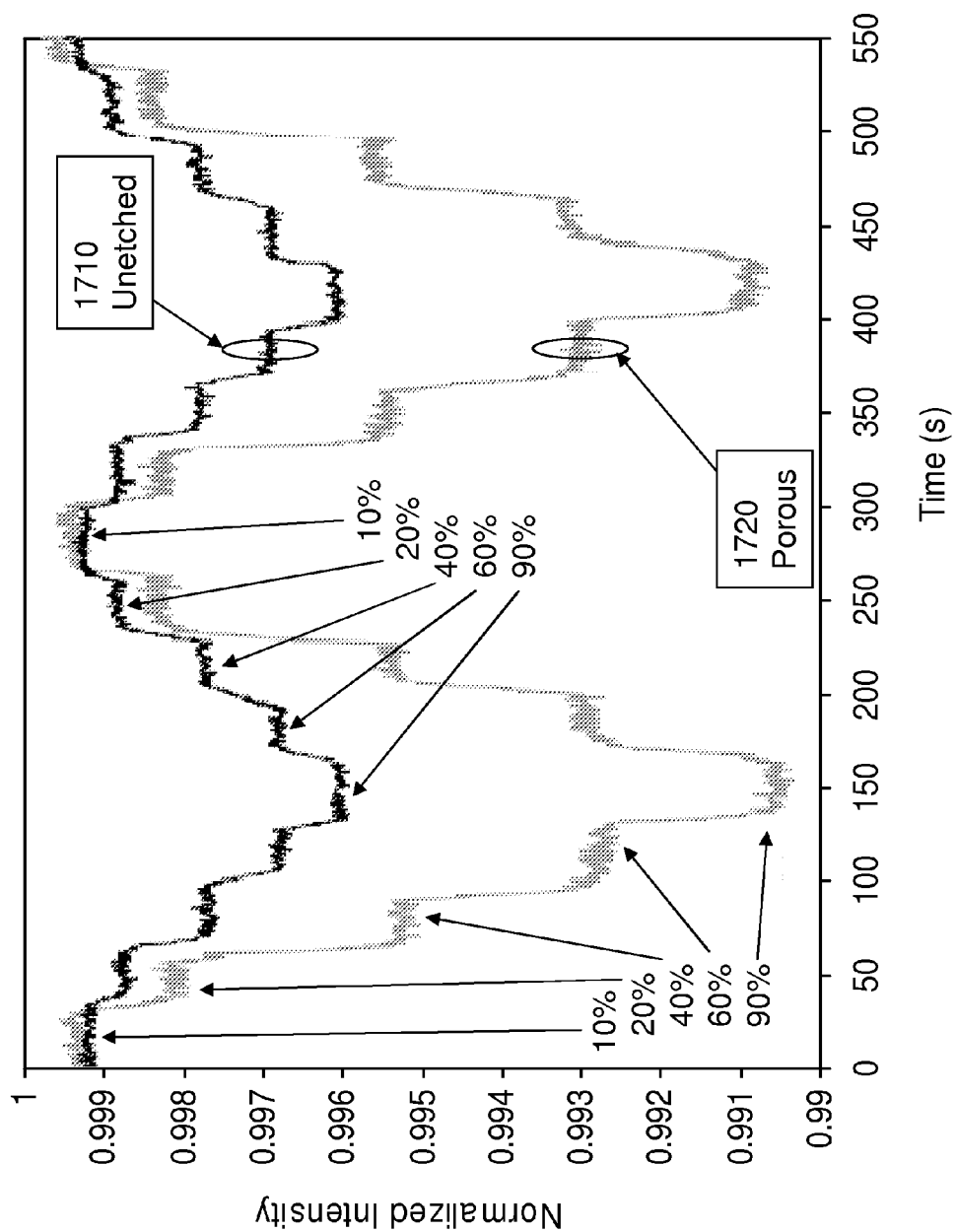

Now referring to FIG. 17 the oxygen sensor results for both unpolished silicon wafer, first response curve 1710, and porous silicon wafer, second response curve 1720, are shown for varying oxygen concentration. In order to obtain first and second response curves 1710 and 1720 respectively the samples were placed in a test chamber with regulated supply of gaseous oxygen and nitrogen. A blue LED ($\lambda_{peak}$=470 nm) placed at 30° to the xerogel coated porous silicon sample is used as the excitation signal. The resulting optical signal is directly detected using a standard photodiode placed parallel to the silicon substrate and recorded by a lock-in amplifier as the gaseous oxygen (O2) level was changed relative to gaseous nitrogen (N2) concentration at oxygen levels of 10%, 20%, 40%, 60% and 90%.

MONOLITHICALLY INTEGRATED OPTO-ELECTRONIC PROBES WITH OPTICAL INTERROGATION: In the preceding sections according to embodiments of the invention as described in respect of FIGS. 1A through 17 the combination of porous silicon, porous polymers, porous membranes, silicon optical waveguide interfaced optical biosensors, and electrical measurements through recording sites upon a silicon substrate offer a path for the monolithic integration of these elements to provide multi-functional, compact, low cost biosensors. Further, the approaches described supra in respect of the embodiments of the invention are compatible with providing such porous materials, membranes, sensors etc as post-fabrication steps to silicon CMOS electronics such that integration of CMOS control, excitation, measurement, and analysis elements may be provided. With optically interrogated biosensors it is necessary to provide optical source(s) and photodetector(s). Porous silicon itself has been demonstrated as an emitter, see for example J. Lin et al "Ultraviolet Light Emission from Oxidized Porous Silicon" (Solid State Communications, Vol. 97, No 3, pp 221-224, 1996), which is compatible with the absorption window for xerogel based biosensors and PIN silicon photodetectors (http://en.wikipedia.org/wiki/Photodiode) that operate within the emission window of these xerogel based biosensors in the visible wavelength range of 400-700 nm.

Such a monolithic optical biosensor is shown in FIG. 18A wherein a biosensor 1800 is shown comprising an optical emitter 1810 which is coupled to first waveguide 1820 and therein through a Y-junction combiner to second optical waveguide 1830 which couples to biosensor 1840. Light coupled from the optical emitter 1810 to the biosensor 1840 excites the active sensing materials within the biosensor 1840 which then emit optical signals upon collision quenching with their chemical species, for example oxygen, $Na^+$, $K^+$. These emitted optical signals are coupled to second optical waveguide 1830 and therein through the Y-junction to fourth optical waveguide 1850. Disposed with the fourth optical waveguide 1850 is optical wavelength filter 1860 which acts as a wavelength filter for emitted optical signals such that only those relating to the optical biosensor are coupled to the photodetector 1870.

The optical filter 1860 may for example be a porous silicon optical filter, see V. Kochergin et al in "Macroporous Silicon Deep UV Filters" (Proc. Earth-Sun System Technology Conference 2005, Paper B1 http://esto.nasa.gov/conferences/estc2005/papers/blp5.pdf). Similarly the optical emitter 1810 may be implemented using porous silicon such as reported by A. Janshoff et al in "Macroporous p-Type Silicon Fabry-Perot Layers. Fabrication, Characterization, and Applications in Biosensing" (J. Am Chem. Soc, No. 120, pp 12108-12116, 1998) (http://www.uni-mainz.de/FB/Chemie/AK-Janshoff/Paper/porous-silicon.pdf)

It would be apparent that monolithically integrated silicon optical emitters and photodetectors may not provide the appropriate emissivity/responsivity for all biosensor elements. As such it would be possible to integrate in a hybrid manner the optical source(s) and photodetector(s). One potential embodiment of this approach is shown in FIGS. 18B and 18C wherein the optical emitter 1810 and photodetector 1870 may be formed using fused semiconductor wafer bonding to the silicon substrate and subsequent processing such that the optical emitter 1810 and photodetector 1870 are evanescently coupled to a silicon-on-insulator waveguide structure, and in the case of the optical emitter 1810 the laser cavity is defined entirely within the silicon-on-insulator waveguide. Similarly the photodetector 1870 may be implemented with other materials such as germanium, see for example L. Chen et al in "High Performance Germanium Photodetectors Integrated on Sub-Micron Silicon Waveguides by Low Temperature Wafer Binding" (Optics Express, Vol. 16 No. 15, pp 11513-11518, July 1998) (http://nanophotonics.ece.cornell.edu/Publications/High%20performance%20germanium%20photodetectors.pdf)

Referring to FIG. 18B there is shown an evanescent AlGaInAs-silicon photodetector according to H. Park et al in "A Hybrid AlGaInAs-Silicon Evanescent Preamplifier and Photodetector" (Optics Express, Vol. 15 No. 21, pp 13539-13546, October 2007 http://www.ece.ucsb.edu/uoeg/publications/papers/park_07_opex_2.pdf). The silicon-on-insulator (SOI) structure 1872 comprises a core region 1876 that has bonded upon it an AlGaInAs photodetector 1874. The AlGaInAs photodetector 1874 having been grown atop an InP substrate was inverted and transferred to the patterned SOI wafer through low temperature plasma assisted wafer bonding performed at 300° C. under vacuum for 18 hours. The InP substrate then being removed using an $HCl/H_2O$ etch before Pd/Ti/Pd/Au p-contacts 1874P are formed atop an SU-8 polymer to bias the structure in conjunction with n-contacts 1874N.

Referring to FIG. 18C there is shown an evanescent AlGaInAs-silicon laser according to H. Park et al in "Electrically Pumped Hybrid AlGaInAs-Silicon Evanescent Laser" (Optics Express, Vol. 14 No. 20, pp 9203-9210 http://www.opticsinfobase.org/DirectPDFAccess/99729518-BDB9-137E-CB304CAD55FFE85A__114596.pdf?da=1&id=114596&seq=0&CFID=40526551&CFTOKEN=82350156). As shown a silicon-on-insulator (SOI) structure 1812 with core region 1816 has bonded upon it an AlGaInAs multi-quantum well (MQW) SCH laser 1814. The AlGaInAs MQW SCH laser 1814 having been grown atop an InP substrate was inverted and transferred to the patterned SOI wafer through low temperature plasma assisted wafer bonding performed at 300° C. under vacuum for 18 hours. The InP substrate then being removed using an $HCl/H_2O$ etch before Pd/Ti/Pd/Au p-contacts 1814P are formed atop the multi-quantum well (MQW) SCH laser 1814 allowing the structure to be biased in conjunction with the n-contacts 1814N.

It would be apparent to one skilled in the art that other optical waveguide circuits may be employed to couple the optical emitter and photodetector to the optical waveguide interfaced to the optical biosensor. For example, the optical emitter and photodetector may be coupled to one side of a multi-mode interferometer (MMI) and the optical biosensor coupled to the other side of the MMI. Further whilst in the embodiments supra the optical emitter and photodetector are coupled to the optical biosensor from a single waveguide it would be apparent that other configurations may be employed, including for example waveguides coupled to each of the optical emitter and photodetector which are then coupled to one side of the optical biosensor or to different sides of the optical biosensor. Further where the optical biosensor is provided within an etched silicon structure, such as within FIGS. 1 and 3 the inner surfaces of the etched silicon may be metallized to improve the coupled optical emission to the photodetector.

With the integration of active optical components such as the optical emitter 1810 and photodetector 1870 to a substrate comprising with optical waveguides and optical wavelength filter 1860 by low temperature wafer bonding techniques a variety of optical sources and photodetectors can be employed outside the operating wavelengths of their porous silicon counterparts to work with the particular xerogel biosensor 1840 characteristics. Beneficially such a hybrid optically interrogated biosensor with low temperature processing allows for the integration with silicon CMOS electronics already integrated into the silicon substrate. Such a fully integrated probe being shown in FIG. 19 as probe 1900. As depicted probe 1900 comprises first and second optically interfaced biosensors 1930A and 1930B respectively together with recording sites 1920. Each recording site being electrically connected via traces 1910 to two electronic stimulation and measurement circuits 1950 such that according to the desired function of the probe 1900 electrical stimuli may be applied to the brain via some of the recording sites 1920 and electrical measurements of the brain made at other recording sites 1920.

Similarly the first optically interfaced biosensor 1930A is interfaced to first optoelectronic driver 1960A comprising interfacing circuits for the emitter and photodetector together with any conditioning circuits etc. The second optically interfaced biosensors 1930B is interfaced to a second optoelectronic driver 1960B. All these electrical circuits being interfaced to microprocessor 1940 allowing the probe 1900 to provide the electrical measurements and biosensor readings to the external environment as well as receiving commands for the provisioning of electrical stimuli.

It would be evident to one skilled in the art that whilst the optical biosensors and electrical recording sites have been presented in the embodiments above as being formed upon a single surface of the silicon substrate that these may be provided upon either different surfaces of the substrate or multiple surfaces of the substrate. Additionally these surfaces may include the edges of the substrate as well as the larger front and back surfaces of the substrate allowing three-dimensional probing of neural activity or stimulation of neural activity. It would be evident that the dimensions of the optical waveguides may be reduced from highly multimoded structures to those supporting only a few modes or even a single mode thereby allowing these to be integrated at increased density or even along the thinner edges of the silicon substrates.

Figure 19:
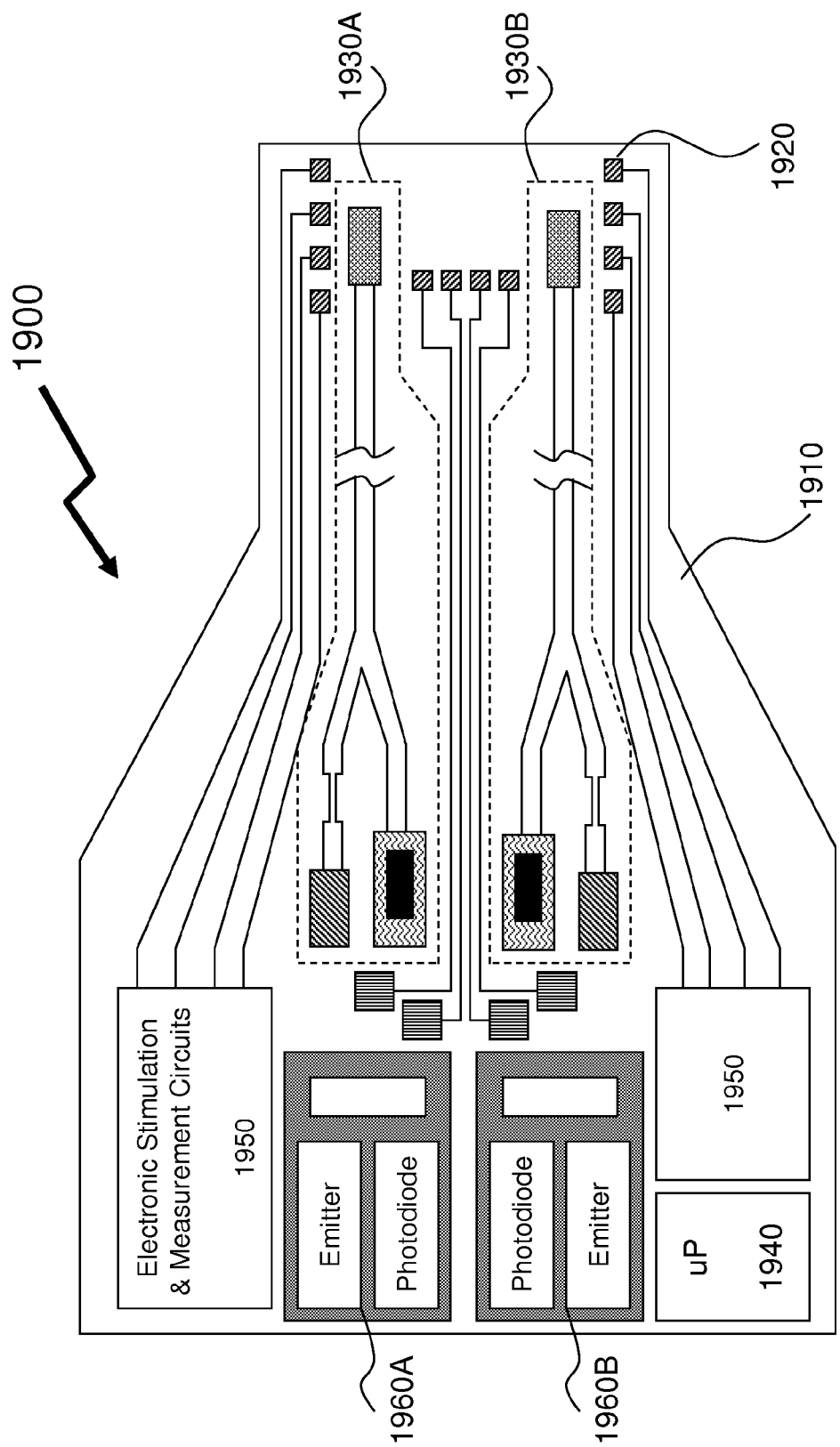
FIG. 19 depicts a monolithic optically interrogated biosensor with low temperature processing and porous silicon structures allowing their integration with silicon CMOS electronics integrated into the silicon substrate according to an embodiment of the invention.

Further whilst the integration of the optoelectronic functionality has been presented in the embodiments presented supra in respect to FIGS. 18 and 19 for a silicon substrate it would be evident that the substrate may be formed from other materials supporting optoelectronic components such as gallium arsenide (GaAs) and indium phosphide (InP) for example. Additionally the silicon based probe may be integrated in a hybrid manner to the optoelectronic elements such as photodetector and optical emitter and electronic interface circuitry. Such embodiments being evident to one skilled in the art.

Additionally the optical biosensors have been discussed primarily from the viewpoint of measuring their optical emission in conjunction with an optical filter, for example to remove the excitation signal from the optical emitter. However, it would be evident that in some devices it would be possible to couple arrays of photodetectors with different wavelength filters to the same optical biosensor or provide a tunable wavelength filter between the biosensor and photodetector or tunable wavelength emitters. Such tunable wavelength filter devices for example being formed from porous silicon and may themselves directly form additional sensing elements, see for example M. Ghulinyan et al in "Free-Standing Porous Silicon Single and Multiple Optical Cavities" (J. Appl. Phys., Vol. 93(12), pp 9724-9729) and S. S. Yun et al in "A Micro-Machined In-Plane Tunable Optical Filter using the Thermo-Optic Effect of Crystalline Silicon" (J. Micromech. Microeng. Vol. 13, pp. 721-725).

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A device comprising;
   a substrate;
   a recording site formed upon a first surface of the substrate comprising at least one of a recording pad and an interconnection electrically connected to the recording pad;
   an optical sensor formed upon a second surface of the substrate comprising at least an optical wave guide and a biosensor; and at least a reinforcement structure, the reinforcement structure formed upon at least a surface of the device to at least one of reduce, distribute, and relocate the stress within the device.

2. A device according to claim 1 wherein;
   the substrate is at least one of silicon, gallium arsenide, indium phosphide, and silica.

3. A device according to claim 1 wherein;
   the substrate is at least one of a thin substrate, an ultra-thin substrate and a substrate epitaxially grown onto a carrier.

4. A device according to claim 1 further comprising:
   at least one of an electrical circuit integrated into the substrate, a CMOS circuit integrated into the substrate, an electrical circuit mounted to the substrate, and a CMOS circuit mounted to the substrate; wherein
   the at least one of is electrically connected to at least one of a bond pad electrically connected to the interconnection, the interconnection and the recording pad.

5. A device according to claim 4 wherein;
   the at least one of is for at least one receiving an electrical signal from and providing an electrical signal to the at least one of the bond pad, the interconnection and the recording pad.

6. A device according to claim 1 wherein;
   the optical waveguide comprises at least one of a polymer waveguide, a silica-on-silicon waveguide, a silicon-on-insulator waveguide and an optical waveguide formed from material epitaxially grown onto the substrate.

7. A device according to claim 1 further comprising:
   at least one of an optical emitter, a photodetector, an optical wavelength filter, and a waveguide circuit for coupling to the biosensor.

8. A device according to claim 7 wherein;
   the at least one of is provided by at least one of processing of the substrate and hybrid integration of the at least one of with the substrate.

9. A device according to claim 7 wherein;
   the at least one of comprises at least a predetermined portion formed from a porous form of the substrate.

10. A device according to claim 7 wherein,
    the at least one is provided by fusing a second substrate to the substrate and processing the resultant structure to form a predetermined portion of the at least one of.

11. A device according to claim 7 further comprising;
    at least one of an electrical circuit integrated within the substrate, a CMOS circuit integrated within the substrate, an electrical circuit mounted to the substrate, and a CMOS circuit mounted to the substrate; wherein the at least one of is electrically connected to at least one of the optical emitter, the photodetector, the optical wavelength filter, and the optical waveguide.

12. A device according to claim 1 wherein;

the bio sensor comprises at least one of a lumiphorous material, a porous material, a xerogel, a protein-doped xerogel, a fluorescent material and a phosphorescent material.

13. A device according to claim 1 wherein;

the bio sensor operates by at least one of fluorescence, phosphorescence, Raman scattering, surface plasmon effect, collision quenching, and absorption.

* * * * *